United States Patent
Yao et al.

(10) Patent No.: US 12,276,625 B2
(45) Date of Patent: Apr. 15, 2025

(54) METHOD FOR SPECIES IDENTIFICATION AND QUALITY DETECTION OF LIQUID-LIKE SAMPLES BASED ON NUCLEAR MAGNETIC RESONANCE TECHNOLOGY

(71) Applicant: EAST CHINA NORMAL UNIVERSITY, Shanghai (CN)

(72) Inventors: Yefeng Yao, Shanghai (CN); Jiachen Wang, Shanghai (CN); Yi Li, Shanghai (CN); Jiaxiang Xin, Shanghai (CN); Jing Zhu, Shanghai (CN); Xuelu Wang, Shanghai (CN)

(73) Assignee: EAST CHINA NORMAL UNIVERSITY, Shanghai (CN)

( * ) Notice: Subject to any disclaimer, the term of this patent is extended or adjusted under 35 U.S.C. 154(b) by 188 days.

(21) Appl. No.: 17/798,389

(22) PCT Filed: Apr. 23, 2021

(86) PCT No.: PCT/CN2021/089234
§ 371 (c)(1),
(2) Date: Aug. 9, 2022

(87) PCT Pub. No.: WO2021/218798
PCT Pub. Date: Nov. 4, 2021

(65) Prior Publication Data
US 2023/0075079 A1    Mar. 9, 2023

(30) Foreign Application Priority Data
Apr. 27, 2020   (CN) .......................... 202010345962.6

(51) Int. Cl.
*G01N 24/08*   (2006.01)
*G01N 33/02*   (2006.01)

(52) U.S. Cl.
CPC ............. *G01N 24/08* (2013.01); *G01N 33/02* (2013.01)

(58) Field of Classification Search
CPC ........ G01N 24/08; G01N 33/02; G01N 33/03; G01N 33/04; G01N 33/14
See application file for complete search history.

(56) References Cited

U.S. PATENT DOCUMENTS

| 4,818,940 A | 4/1989 | Hennig et al. |
| 2007/0055456 A1* | 3/2007 | Raftery ................ G01R 33/465 702/22 |

(Continued)

FOREIGN PATENT DOCUMENTS

| CN | 104198518 A | 12/2014 |
| CN | 105092628 A | 11/2015 |

(Continued)

OTHER PUBLICATIONS

International Search Report, issued in PCT/CN2021/089234, dated Jul. 22, 2021.

(Continued)

*Primary Examiner* — Rodney A Bonnette
(74) *Attorney, Agent, or Firm* — Birch, Stewart, Kolasch & Birch, LLP

(57) ABSTRACT

The present invention is directed to a method of species identification and quality detection of liquid-like samples based on nuclear magnetic resonance technology. In this invention, a two-dimensional relaxation signal containing the 1H T1 and T2 relaxation properties of liquid-like samples is obtained by applying a composite pulse sequence to samples, and from this a fingerprint spectrum is established. The fingerprint spectrum can be associated with the (Continued)

essential characteristics of the tested sample, thus can be used to distinguish a specific liquid-like sample from the others.

8 Claims, 8 Drawing Sheets

(56) References Cited

U.S. PATENT DOCUMENTS

| | | | | |
|---|---|---|---|---|
| 2012/0133358 A1* | 5/2012 | Broz | ................... | G01N 24/084 324/318 |
| 2019/0011383 A1* | 1/2019 | Cohen | .................. | G01N 24/085 |
| 2021/0123894 A1* | 4/2021 | Wang | ....................... | G01N 1/38 |

FOREIGN PATENT DOCUMENTS

| | | |
|---|---|---|
| CN | 108982570 A | 12/2018 |
| CN | 110146537 A | 8/2019 |

OTHER PUBLICATIONS

Written Opinion of the International Searching Authority, issued in PCT/CN2021/089234, dated Jul. 22, 2021.

* cited by examiner

METHOD FOR SPECIES IDENTIFICATION AND QUALITY DETECTION OF LIQUID-LIKE SAMPLES BASED ON NUCLEAR MAGNETIC RESONANCE TECHNOLOGY

This application requires the priority of a Chinese invention patent application whose application date is Apr. 27, 2020, the application number is 202010345962.6, and the invention title is "A method for species identification and quality detection of edible oil based on nuclear magnetic resonance technology".

TECHNICAL FIELD

This present invention relates to the technical field of magnetic resonance technology and liquid identification technology, specifically to a method of species identification and quality detection of liquid-like samples based on nuclear magnetic resonance relaxation technology.

BACKGROUND OF THE INVENTION

Many foods and health products in daily life, such as edible oil, milk, jelly, donkey-hide gelatin, etc., are all in a liquid-like state. At present, species identification and quality detection of liquid-like foods and health products have become an important topic in food safety research. Take edible oil as an example. Edible oil is a necessity in life. Generally speaking, edible oil is composed of a variety of saturated and unsaturated fatty acids, with a unique flavor and rich nutrition. The unsaturated fatty acids (mainly oleic acid) can lower cholesterol, and essential fatty acids (such as linolenic acid, linoleic acid, arachidonic acid, etc.) can soften blood vessels, and thus lower blood lipids and blood pressure, promoting microcirculation. A reasonable intake of fatty acids can provide sufficient energy for the human body, meanwhile effectively preventing various cardiovascular diseases. Edible oil is widely used in daily cooking. China is a major producer and consumer of edible oil, but in order to make huge profits, some illegal traders in the market add lower price or different processing levels of edible oil to normal edible oils and sell the shabby edible oil as the good ones, causing serious damage to health and rights of consumers.

At present, the identification technology of edible oil used in the national standard in China mainly uses sensory experience and physical and chemical detection as preliminary measurement, and then uses gas chromatography to determine the composition of edible oil fatty acid and phytosterols as final identification. There are also some signature marker detection technologies and detection technologies based on a photoelectric sensor. However, the aforementioned methods have their own advantages and disadvantages, and thus it is difficult to meet the requirements of accuracy, stability, multiple measurement and operability at the same time. Meanwhile, the traditional chromatographic, mass spectrometry and optical spectroscopy often require sample pretreatment which destroys the sample during the detection, thus cannot realize non-destructive sample detection. More importantly, the identification technology of edible oil based on traditional chromatography, mass spectrometry, and optical spectroscopy usually rely on large instruments and cannot achieve rapid detection on site.

The existing patent CN108982570A relates to a method for identifying types of edible oil based on nuclear magnetic resonance technology, which is analyzed by the analysis of $^1$H nuclear magnetic resonance spectrum rather than relaxation analysis of edible oil. Accordingly, the method described in the patent CN108982570A has the detection principle which is completely different from that described in the present invention. FIG. 3 shows the hydrogen spectra of five edible oil samples. It can be seen from the figure that there is little difference in the $^1$H nuclear magnetic resonance spectra of different edible oil, and it is difficult to effectively distinguish the types of edible oil through the spectra. Moreover, the method reported in the patent CN108982570A requires a high-resolution nuclear magnetic resonance instrument, which cannot be applied to low-field nuclear magnetic resonance relaxometry. The method in the present invention is applicable not only to high-resolution nuclear magnetic instruments, but also to low-field nuclear magnetic resonance relaxometry. Therefore, the method in the present invention applies to different instruments from that in the patent CN108982570A.

In the existing literature (Xin Wang et al., Food and Fermentation Industry 2011, 37, 177-181, DOI: 10.13995/j.cnki.11-1802/ts.2011.03.020; Xin Wang et al., Food Industry Science and Technology 2014, 12, 58-65; DOI: 10.13386/j.issn1002-0306.2014.12.003), comparison of different edible oils and adulterated identification are achieved by measuring $^1$H $T_2$ relaxation properties of edible oils. The method can be used in the existing low-field and high-field magnetic resonance instruments. However, the method uses $^1$H $T_2$ relaxation properties of the system under test obtained by the conventional method (i.e., CPMG sequence). From the experimental data, the $^1$H $T_2$ relaxation properties of edible oil alone cannot be used to effectively distinguish different edible oils and the edible oil adulteration.

In addition, the adulteration of cow and goat milk, the mixing of different quality of donkey-hide gelatin, and the distinction of scorpion samples from different places of origin are also important issues related to foods and drugs safety, thus it is urgent to find a simple and fast method to distinguish similar samples.

SUMMARY OF THE INVENTION

In order to overcome the defects of current technologies, the present invention provides a method that utilizes the relaxation properties of liquid-like samples by amplifying the differences of relaxation properties to achieve species identification and quality detection of liquid-like samples. Firstly, edible oil is taken as an example to illustrate the content of the invention. The main chemical components in edible oils are various saturated and unsaturated fatty acids. The chemical structures of these saturated and unsaturated fatty acids are similar, but the types, contents, and relative proportions vary with different types of edible oils. Since different saturated and unsaturated fatty acids have different nuclear magnetic relaxation properties, this feature can be used for species identification and quality detection of edible oil. Similarly, the examples of the present invention show that the distinction of cow and goat milk, different donkey-hide gelatin or scorpions from different places of origin can also be achieved by using this method.

The present invention develops a method for species identification and quality detection of liquid-like samples based on nuclear magnetic resonance relaxation technology. The core design idea of this method is to amplify the differences in nuclear magnetic resonance relaxation properties of different liquid-like samples by designing a new nuclear magnetic resonance method to measure two-dimensional data set containing $^1$H $T_1$ and $T_2$ relaxation properties of liquid-like samples, thus realizing species identification and quality detection of liquid-like samples. Meanwhile, the present invention can realize non-destructive testing of samples without sample pretreatment. The method of the present invention can be implemented on a low-field magnetic resonance instrument which can achieve rapid on-site detection by moving on-board.

A more specific method comprises the following steps:

Step 1: Designing a pulse sequence that includes pulse block or composite pulses containing $^1$H spin-echo function and pulse block or composite pulses containing $T_1$ filter function;

Step 2: Applying pulse sequence to the targeted liquid-like samples to obtain their $^1$H two-dimensional relaxation signals;

Step 3: Converting the obtained $^1$H two-dimensional relaxation signals into fingerprint spectra of the targeted liquid-like samples, so as to be used for species identification and quality detection of liquid-like samples.

Wherein the liquid-like samples refer to liquid and gel substances with a certain fluidity, including edible oil, cow and goat milk, donkey-hide gelatin, scorpion powder solution, yogurt, beverages, oils in general, etc.

In Step 1 of the present invention, the pulse sequence comprises the following designs and the sub-steps:

Step 1-1: Using a pulse block or composite pulses to excite $^1$H magnetic resonance signal of the system under test;

Step 1-2: Applying the pulse block or the composite pulses containing $^1$H spin-echo function to the system under test, and the pulse block or the composite pulses may contain one or more variables;

Step 1-3: Applying the pulse block or the composite pulses containing $^1$H $T_1$ filter function to the system under test, and the pulse block or the composite pulses may contain one or more variables;

Step 1-4: Converting the $^1$H magnetic resonance signal of the targeted samples into a signal detectable by magnetic resonance instrument through the pulse block or the composite pulses, and then collecting the signals.

In the pulse sequence in the present invention:

The first step: Exciting the $^1$H magnetic resonance signal of the system under test with a 90° pulse with a phase of x;

The second step: Applying the composite pulse block) $[\tau_1-(180°)_y-\tau_1]_n$, wherein n is the number of repetitions, on the system under test. The composite pulse block includes the time variable $\tau_1$ and the number repetition variable n;

The third step: Applying the composite pulse block) $[\tau_2-(90°)_x-\tau_3]$ to the system under test, wherein $\tau_2$ is the time constant ranging from 10 us to 20 μs, and $\tau_3$ is the time variable;

The fourth step: Converting the $^1$H magnetic resonance signal of the system under test into a signal detectable by magnetic resonance instrument with a 90° pulse with the phases of x, y, −x, −y, and then collecting the signals.

In Step 2 of the present invention, the $^1$H two-dimensional relaxation signal of the targeted sample can be obtained by controlling the variables in the pulse block or the composite pulses containing $^1$H spin-echo function and the variables in the pulse block or the composite pulses containing $\tau_1$ filter function in the pulse sequence.

In Step 3 of the present invention, $f_n(x,y)$ is obtained by normalizing the signal intensity of the above-mentioned two-dimensional relaxation signal $f(x,y)$; the fingerprint spectrum can be obtained by subtracting the reference function $F(x,y)$ from $f_n(x,y)$; the said reference function $F(x,y)$ is obtained by designing according to the $^1$H relaxation properties of the target sample, or performing surface fitting of $f_n(x,y)$, or averaging $F_m(x, y)$, m=1, 2, ..., i, which is acquired from surface fitting of the multiple two-dimensional relaxation signals.

In the present invention, when comparing the fingerprint spectrum for species identification and quality detection of liquid-like samples of the same type, the same reference function is used in the generation process of fingerprint spectrum in Step 3 for those belonging to the same sample type but in different qualities.

In the present invention, when using the above-mentioned pulse sequence to acquire the two-dimensional relaxation signal of corn germ oil, the two-dimensional relaxation signal of corn germ oil, $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the t2 distribution fingerprint spectrum of corn germ oil is obtained by subtracting the selected reference function $F(x, y)$ from the normalized $f(\tau_1, n)$; and/or, When using the above-mentioned pulse sequence to acquire the two-dimensional relaxation signal of peanut oil, the two-dimensional relaxation signal of peanut oil $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the $\tau_2$ distribution fingerprint spectrum of peanut oil is obtained by subtracting the selected reference function $F(x, y)$ from the normalized $f(\tau_1, n)$; and/or, When using the above-mentioned pulse sequence to acquire the two-dimensional relaxation signal of soybean oil, the two-dimensional relaxation signal of soybean oil $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the $\tau_2$ distribution fingerprint spectrum of soy bean oil is obtained by subtracting the selected reference function $F(x, y)$ from the normalized $f(\tau_1, n)$; and/or, When using the above-mentioned pulse sequence to acquire the two-dimensional relaxation signal of linseed oil, the two-dimensional relaxation signal of linseed oil $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the $\tau_2$ distribution fingerprint spectrum of linseed oil is obtained by subtracting the selected reference function $F(x, y)$ from the normalized $f(\tau_1, n)$; and/or, When using the above-mentioned pulse sequence to acquire the two-dimensional relaxation signal of olive oil, the two-dimensional relaxation signal of olive oil $f(\tau_1, n)$ can be obtained by fixing $\tau_3$ and changing $\tau_1$ and n, wherein $\tau_1$ is a set of time values and n is cycle number, $f(\tau_1, n)$ is the signal intensity corresponding to $\tau_1$ and n; the $\tau_2$ distribution fingerprint spectrum of olive oil is obtained by subtracting the selected reference function $F(x, y)$ from the normalized $f(\tau_1, n)$; and/or, When using the above-mentioned pulse sequence to acquire the two-dimensional relaxation signal of the commercially available cow milk, the two-dimensional relaxation signal of the commercially available cow milk $f(\tau_1, n)$ can be obtained by fixing $\tau_3$ and changing $\tau_1$ and n, wherein $\tau_1$ is a set of time values, n is a set of cycle number, $f(\tau_1, n)$ is the signal intensity corresponding to $\tau_1$ and n; the $\tau_2$ distribution fingerprint spectrum of the commercially available cow milk is obtained by subtracting the selected reference function $F(x, y)$ from the normalized $f(\tau_1, n)$; and/or, When using the above-mentioned pulse sequence to acquire the two-dimensional relaxation signal of the commercially available goat milk, the two-dimensional relaxation signal of the commercially available goat milk $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the $t_2$ distribution fingerprint spectrum of the commercially available goat milk is obtained by subtracting the selected reference function $F(x, y)$ from the normalized $f(\tau_1, n)$; and/or, When using the above-mentioned pulse sequence to acquire the two-dimensional relaxation signal of pig hide gelatin, the two-dimensional relaxation signal of pig hide gelatin $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the t2 distribution fingerprint spectrum of pig hide gelatin is obtained by subtracting the selected reference function $F(x, y)$ from the normalized $f(\tau_1, n)$; and/or, When using the above-mentioned pulse sequence to acquire the two-dimensional relaxation signal of cow hide gelatin, the two-dimensional relaxation signal of cow hide gelatin $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the t2 distribution fingerprint spectrum of cow hide gelatin is obtained by subtracting the selected reference function $F(x, y)$ from the normalized $f(\tau_1, n)$; and/or, When using the above-mentioned pulse sequence to acquire the two-dimensional relaxation signal of Liaoning scorpion powder solution, the two-dimensional relaxation signal of Liaoning scorpion powder solution $f(\tau_1, n)$ can be obtained by fixing $\tau_3$ and changing $\tau_1$ and n, wherein $\tau_1$ is a set of time values and n is cycle number, $f(\tau_1, n)$ is the signal intensity corresponding to $\tau_1$ and n; the t2 distribution fingerprint spectrum of Liaoning scorpion powder solution is obtained by subtracting the selected reference function $F(x, y)$ from the normalized $f(\tau_1, n)$; and/or, When using the above-mentioned pulse sequence to acquire the two-dimensional relaxation signal of Shanxi scorpion powder solution, the two-dimensional relaxation signal of Shanxi scorpion powder solution $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the t2 distribution fingerprint spectrum of Shanxi scorpion powder solution is obtained by subtracting the selected reference function $F(x, y)$ from the normalized $f(\tau_1, n)$.

In the present invention, when using the above-mentioned pulse sequence to acquire the two-dimensional relaxation signal of corn germ oil, the two-dimensional relaxation signal of corn germ oil $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of corn germ oil is obtained by subtracting the selected reference function $F_a(x, y)$ from the normalized $f_a(\tau_3, n)$; and/or, When using the above-mentioned pulse sequence to acquire the two-dimensional relaxation signal of peanut oil, the two-dimensional relaxation signal of peanut oil $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $\tau_1$-$\tau_2$ correlation fingerprint spectrum of peanut oil is obtained by subtracting the selected reference function $F_a(x, y)$ from the normalized $f_a(\tau_3, n)$; and/or, When using the above-mentioned pulse sequence to acquire the two-dimensional relaxation signal of soybean oil, the two-dimensional relaxation signal of soybean oil $f_a(\tau_3, n)$ can be obtained by fixing $\tau_1$ and changing $\tau_3$ and n, wherein $\tau_3$ is a set of time values, n is cycle number. $f_a(\tau_3, n)$ is the signal intensity corresponding to $\tau_3$ and n; the $t_1$-$t_2$ correlation fingerprint spectrum of soybean oil is obtained by subtracting the selected reference function $F_a(x, y)$ from the normalized $f_a(\tau_3, n)$; and/or, When using the above-mentioned pulse sequence to acquire the two-dimensional relaxation signal of linseed oil, the two-dimensional relaxation signal of linseed oil $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of linseed oil is obtained by subtracting the selected reference function $F_a(x, y)$ from the normalized $f_a(\tau_3, n)$; and/or, When using the above-mentioned pulse sequence to acquire the two-dimensional relaxation signal of olive oil, the two-dimensional relaxation signal of olive oil $f_a(\tau_3, n)$ can be obtained by fixing $\tau_1$ and meanwhile changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of olive oil is obtained by subtracting the selected reference function $F_a(x, y)$ from the normalized $f_a(\tau_3, n)$; and/or, When using the above-mentioned pulse sequence to acquire the two-dimensional relaxation signal of the corn germ oil sample mixed with 1% water by weight, the two-dimensional relaxation signal of the corn germ oil sample mixed with 1% water by weight $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of the corn germ oil sample mixed with 1% water by weight is obtained by subtracting the selected reference function $F_a(x, y)$ from the normalized $f_a(\tau_3, n)$; and/or, When using the above-mentioned pulse sequence to acquire the two-dimensional relaxation signal of the corn germ oil sample mixed with 1% lard by weight, the two-dimensional relaxation signal of the corn germ oil sample mixed with 1% lard by weight $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of the corn germ oil sample mixed with 1% lard by weight is obtained by subtracting the selected reference function $F_a(x, y)$ from the normalized $f_a(\tau_3, n)$; and/or, When using the above-mentioned pulse sequence to acquire the two-dimensional relaxation signal of the corn germ oil sample mixed with 1% beef tallow by weight, the two-dimensional relaxation signal of the corn germ oil sample mixed with 1% beef tallow by weight $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of the corn germ oil sample mixed with 1% beef tallow by weight is obtained by subtracting the selected reference function $F_a(x, y)$ from the normalized $f_a(\tau_3, n)$; and/or, When using the above-mentioned pulse sequence to acquire the two-dimensional relaxation signal of the corn germ oil sample mixed with 1% butter by weight, the two-dimensional relaxation signal of the corn germ oil sample mixed with 1% butter by weight $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of the corn germ oil sample mixed with 1% butter by weight is obtained by subtracting the selected reference function $F_a(x, y)$ from the normalized $f_a(\tau_3, n)$.

There are two important technical features in the present invention:
1. The above-mentioned pulse sequence and its data acquisition scheme—this is a newly designed pulse sequence and data acquisition scheme, which can be used to measure two-dimensional data containing $^1H$ $T_1$ and $T_2$ relaxation properties of edible oils or other liquid-like samples, and amplify $^1H$ $T_1$ and $T_2$ relaxation differences of different edible oils or other liquid-like samples;
2. Data processing method (subtracting the reference function from two-dimensional data to obtain the fingerprint spectrum and its variants)—this is a newly developed data processing method. The fingerprint spectrum obtained by this method can be used as a standard to distinguish different types of edible oils or other liquid-like samples, and its digital form is very suitable for constructing the big data of edible oils or other liquid-like samples and authenticity judgments based on artificial intelligence.

The present invention has innovative ideas which are different from previous inventions and documentary works:
1. Based on the feature that $^1H$ $T_1$ and $T_2$ relaxation properties are different in edible oils or other liquid-like samples, the method in the present invention breaks through the limitation of using only $^1H$ $T_2$ relaxation to detect and identify edible oils or other liquid-like samples in previous works, meanwhile, innovatively proposes to amplify $^1H$ $T_1$ and $T_2$ relaxation differences of different edible oils or other liquid-like samples by measuring two-dimensional $^1H$ $T_1$ and $T_2$ relaxation data containing relaxation properties of edible oils or other liquid-like samples, thus realizing detection and identification of different edible oils or other liquid-like samples;
2. Based on the above-mentioned idea, a new pulse sequence, and the corresponding data acquisition method are developed to be used to amplify $^1H$ $T_1$ and $T_2$ relaxation differences of different edible oils or other liquid-like samples;
3. A "fingerprint spectrum" containing $^1H$ $T_1$ and $T_2$ relaxation properties of edible oil or other liquid-like samples is established. The fingerprint spectrum can be used as a standard to distinguish different types of edible oils or other liquid-like samples, meanwhile, its digital form is very suitable for constructing the big data of edible oils or other liquid-like samples and authenticity judgments based on artificial intelligence.
4. The method in the present invention can be used in high-resolution nuclear magnetic instruments and low-field magnetic resonance relaxometry, overcoming the dependence of patent CN108982570A on nuclear magnetic resonance signal resolution. At the same time, the measurement of $^1H$ $T_1$ and $T_2$ relaxation properties overcomes low discrimination caused by only measuring $^1H$ $T_2$ relaxation measurement in traditional methods.
5. Compared with the traditional chromatographic, mass spectrometry and optical spectroscopy, the method in the present invention can realize a non-destructive sample testing without sample pretreatment. The method in the present invention can be implemented on a low-field magnetic resonance instrument which can realize rapid on-site detection by moving on board.

In the existing reports, there are two methods for detecting and identifying edible oil by using nuclear magnetic resonance. One is to detect and identify edible oils by using high-resolution magnetic resonance spectroscopy (the existing patent CN108982570A). The principle of this method is based on the recognition of molecular signals of edible oils in a high-resolution magnetic resonance spectrum, thus it relies on a high-resolution nuclear magnetic resonance spectrometer. Because a high-resolution nuclear magnetic resonance spectrometer is usually too bulky to move, the method described in the patent CN108982570A usually cannot achieve quick on-site detection of edible oils. Meanwhile, in the practical operation, the method described in the patent CN108982570A is not easy to effectively distinguish the different edible oils (FIG. 3). The method described in the present invention overcomes the limitation of the patent CN108982570A which requires the use of a high-resolution nuclear magnetic spectrometer and has low discrimination between different edible oils. The other is a nuclear magnetic resonance method for detecting and identifying edible oil to detect and identify edible oils by comparing the $^1H$ $T_2$ relaxation properties differences. This method uses $^1H$ $T_2$ relaxation properties obtained by the conventional nuclear magnetic resonance method (CPMG sequence), which can be used on low-field and high-field magnetic resonance instruments. From the experimental data, there is no big difference in $^1H$ $T_2$ relaxation properties of different edible oils. This method does not have good discrimination for different edible oils (Xin Wang et al., Food and Fermentation Industry 2011, 37, 177-181, DOI: 10.13995/j.cnki.11-1802/ts.2011.03.020; Xin Wang et al., Journal of Food Safety and Quality Inspection 2013, 4, 1428-1436; DOI: 10.19812/j.cnki.jfsq11-5956/ts.2013.05.026). The method in the present invention is based on the feature that different edible oils have different properties of $^1H$ $T_1$ and $T_2$ relaxation, breaking through limitations of using only $^1H$ $T_2$ for species identification and quality detection of edible oils in previous works, and innovatively proposing to amplify $^1H$ $T_1$ and $T_2$ relaxation differences of different edible oils or other liquid-like samples by measuring two-dimensional data containing $^1H$ $T_1$ and $T_2$ relaxation properties, thus realizing detection and identification of different edible oils. Based on the above-mentioned idea, the present invention has developed a new pulse sequence and the corresponding data acquisition method that can amplify the difference in $^1H$ $T_1$ and $T_2$ relaxation properties of different edible oils. For the above-mentioned relaxation data, the present invention has developed a data processing method and constructed a 'fingerprint spectrum' containing $^1H$ $T_1$ and $T_2$ relaxation properties of edible oils. The method of the present invention can be used on high-resolution nuclear magnetic spectrometers and low-field nuclear magnetic resonance relaxometry, which overcomes the dependence of the patent CN108982570A on nuclear magnetic signal resolution. At the same time, by measuring $^1H$ $T_1$ and $T_2$ relaxation properties, it overcomes low discrimination of the traditional method caused by measuring only $^1H$ $T_2$ relaxation. Meanwhile, the fingerprint spectrum proposed by the present invention can not only be used as a standard to distinguish different types of edible oils, but also its digital form is very suitable for constructing big data of edible oils and authenticity judgments based on artificial intelligence. In summary, the present invention amplifies $^1H$ $T_1$ and $T_2$ relaxation differences of different edible oils by designing a new pulse sequence and corresponding data acquisition method, thus realize species identification and quality detection of edible oils. The method in the present invention has good accuracy, sensitivity and reproducibility. Meanwhile, the present invention can not only be applied to species identification and quality detection of edible oil, but also to species identification and quality detection of liquid-like samples such as cow or goat milk, donkey-hide gelatin, scorpion powder slurry solution, yogurt, beverages, and oils in general. The present invention has the advantages of rapid detection, no need for sample pretreatment, no need to destroy the sample before and after detection and rapid on-site inspection of edible oil or other liquid samples by moving on board when combined with low-field nuclear magnetic resonance relaxometry, which is a new and original technology.

PREFERRED EMBODIMENTS OF THE INVENTION

The following examples are given to further illustrate the specific solutions of the present invention. The implementation of the present invention process, including the conditions, experimental methods, etc., are common knowledge and known knowledge in the field. The present invention has no special limitations. Meanwhile, the embodiments are only used to illustrate the present invention and not to limit the scope of the present invention.

The invention discloses a method based on nuclear magnetic resonance technology that can carry out species identification and quality detection of liquid-like samples. The present invention applies a specially designed combined pulse sequence to liquid-like sample to obtain a two-dimensional relaxation signal containing the $^1H$ $T_1$ and $T_2$ relaxation characteristics of the sample, which breaks through the weakness of the traditional methods that only uses $^1H$ $T_2$ and cannot effectively distinguish different liquid-like samples. From the two-dimensional relaxation signal, the fingerprint of the liquid-like sample can be established. The fingerprint spectrum is related to the essential characteristics of the liquid-like sample, and can be used as a standard for distinguishing a specific liquid-like sample from the others. Meanwhile, the digital form of the fingerprint spectrum obtained by the present invention is very suitable for constructing the big data of a sample and the quality detection and authenticity judgment of a sample based on artificial intelligence. This method has the characteristics of no need for pretreatment of the test sample, and non-destructive testing of the test object. It also has the advantages of convenience and quickness, strong operability, good stability and reproducibility, etc., and can be used for the identification of a variety of fluid samples. And quality inspection, has a wide range of application value.

Figure 1:
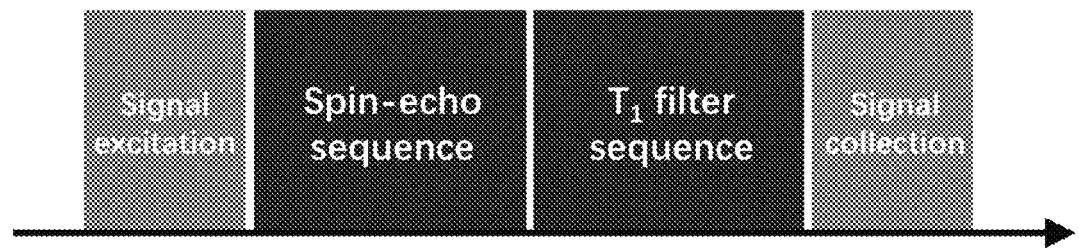
FIG. 1: A schematic diagram of the pulse sequence used to acquire fingerprint spectrum of edible oils or other liquid-like samples.

The main steps of the implementation process are as follows:

Step 1: Designing a pulse sequence that includes pulse block or composite pulses containing $^1H$ spin-echo function and pulse block or composite pulses containing $T_1$ filter function. The scheme of pulse sequence is referred to FIG. 1;

Step 2: Applying the pulse sequence obtained from Step 1 to the targeted liquid-like samples to obtain their $^1H$ two-dimensional relaxation signals of the targeted liquid-like samples;

Step 3: Converting the obtained $^1H$ two-dimensional relaxation signals from Step 2 into the fingerprint spectrum of the targeted liquid-like samples, so as to be used for species identification and quality detection of edible oil or the liquid-like samples.

Wherein, the said liquid-like samples refer to liquid and gel substances with a certain fluidity, including edible oil, cow and goat milk, donkey-hide gelatin, scorpion powder solution, yogurt, beverages, oils in general, etc.

In Step 1 of the present invention, the pulse sequence comprises the following designs and the sub-steps:

Step 1-1: Using a pulse block or composite pulses to excite $^1H$ magnetic resonance signal of the system under test; Step 1-2: Applying the pulse block or the composite pulses containing $^1H$ spin-echo function to the system under test, and the pulse block or the composite pulses may contain one or more variables; Step 1-3: Applying the pulse block or the composite pulses containing $^1H$ $T_1$ filter function to the system under test, and the pulse block or the composite pulses may contain one or more variables; Step 1-4: Converting the $^1H$ magnetic resonance signal of the targeted samples into a signal detectable by the magnetic resonance instrument through the pulse block or the composite pulses, and then collecting the signals.

Figure 2:
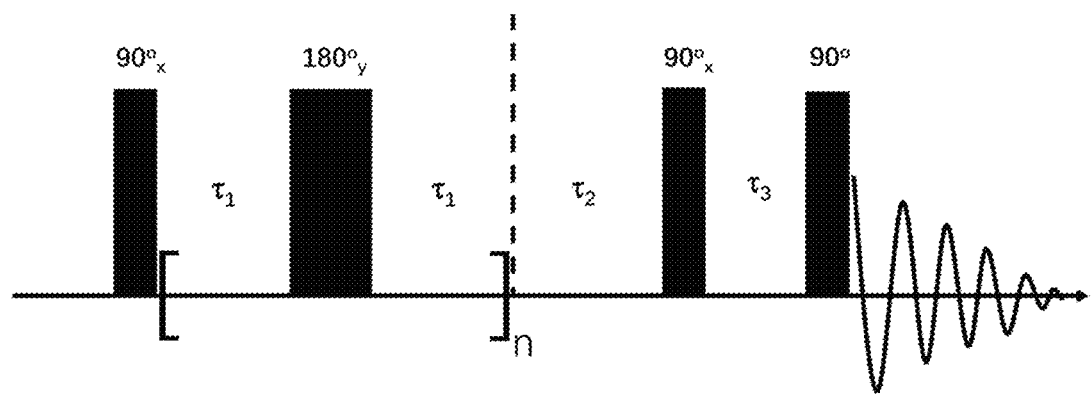
FIG. 2: Example of a pulse sequence used to acquire fingerprint spectrum of edible oils or other liquid-like samples.
Figure 3:
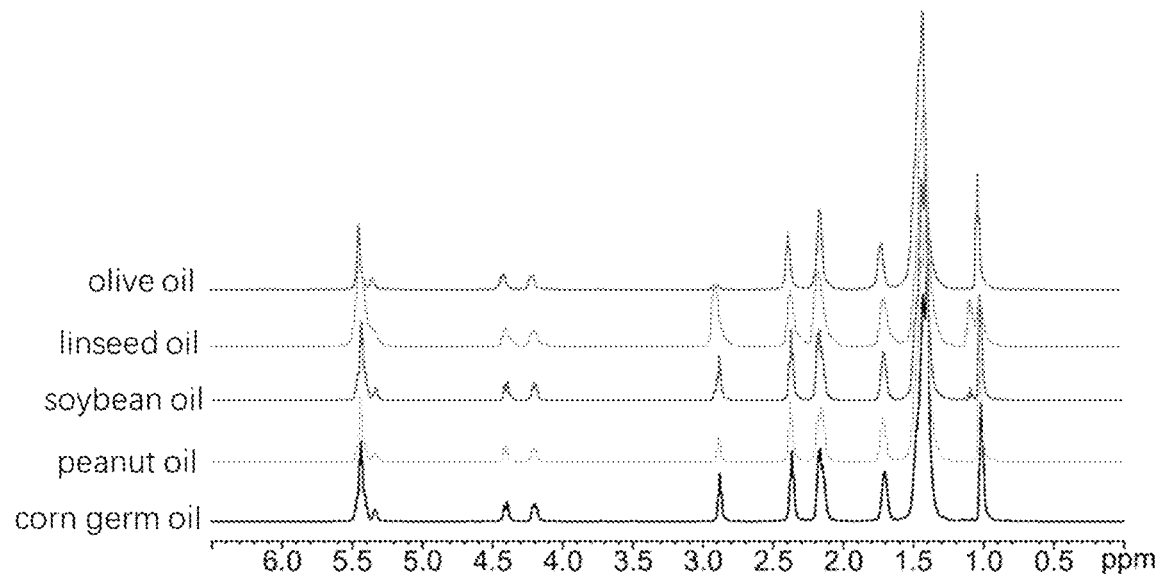
FIG. 3: High-resolution $^1H$ NMR spectrum of corn germ oil, peanut oil, soybean oil, linseed oil and olive oil samples with Bruker 500 M NMR spectrometer.

FIG. 2 shows an example of the above-mentioned pulse sequence which can be used to obtain the two-dimensional relaxation signal of edible oil. In this pulse sequence, there are four steps: The first step: exciting the $^1H$ magnetic resonance signal of the system under test with a 90° pulse with a phase of x; The second step: Applying the composite pulse block) $[\tau_1-(180°)_y-\tau_1]_n$, which comprises the time variable $\tau_1$ and the number repetition variable n; The third step: Applying the composite pulse block $[\tau_2-(90°)_x-\tau_3]$ to the system under test, wherein $\tau_2$ is the time constant ranging from 10 μs to 20 μs, and $\tau_3$ is the time variable; The fourth step: Converting the $^1H$ magnetic resonance signal of the system under test into a signal detectable by the magnetic resonance instrument with a 90° pulse with the phases of x, y, −x, −y, and then collecting the signals.

In Step 2 of the present invention, the $^1H$ two-dimensional relaxation signal of the targeted sample can be obtained by controlling the variables in the pulse block or the composite pulses containing the $^1H$ spin-echo function and the variables in the pulse block or the composite pulses containing $\tau_1$ filter function in the pulse sequence. Through the design of the variables, different types of two-dimensional relaxation signal can be obtained.

In Step 3 of the present invention, $f_n(x,y)$ is obtained by normalizing the signal intensity of the above-mentioned two-dimensional relaxation signal f(x,y); the fingerprint spectrum can be obtained by subtracting the reference function F(x,y) from $f_n(x,y)$; the reference function F(x,y) is obtained by designing according to the $^1H$ relaxation properties of the target sample, or performing surface fitting of $f_n(x,y)$, or averaging $F_m(x, y)$, m=1, 2, . . . , i, which is acquired from surface fitting of the multiple two-dimensional relaxation signals.

In the present invention, when comparing the fingerprint spectrum for species identification and quality detection of liquid-like samples of the same type, the same reference function is used in the generation process of fingerprint spectrum in Step 3 for those belonging to the same sample type but in different quality.

Figure 4:
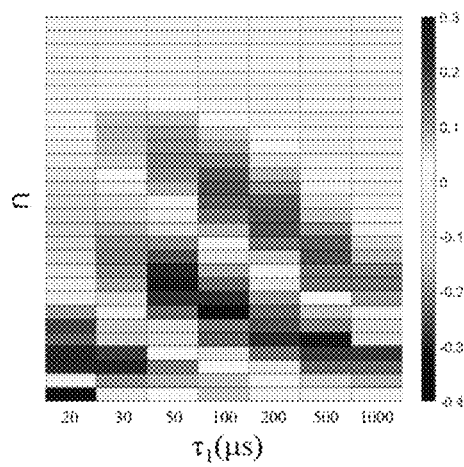
FIG. 4: The t2 distribution fingerprint spectrum of a corn germ oil sample.

FIG. 4 shows an example of the $t_2$ distribution fingerprint spectrum of a corn germ oil sample. The pulse sequence shown in FIG. 2 was used to acquire the two-dimensional relaxation signal of the corn germ oil sample. The two-dimensional relaxation signal of corn germ oil, $f(\tau_1, n)$, was obtained by fixing $\tau_3$ and changing $\tau_1$ and n, wherein $\tau_1$ is a set of time values, n is cycle number, and $f(\tau_1, n)$ is the signal intensity corresponding to $\tau_1$ and n. The reference function F(x, y) is obtained by performing surface fitting of $f(\tau_1, n)$. The t2 distribution fingerprint spectrum of corn germ oil in FIG. 4 was obtained by subtracting the selected reference function F(x, y) from the normalized $f(\tau_1, n)$.

Figure 5:
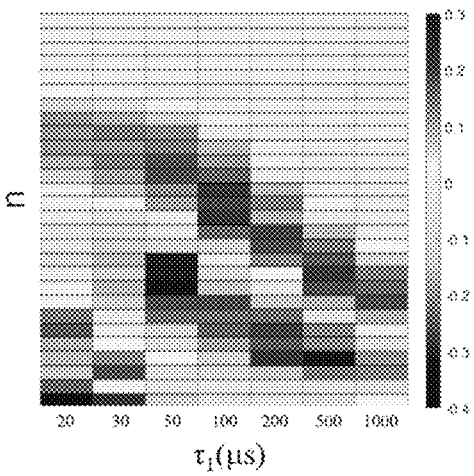
FIG. 5: The t2 distribution fingerprint spectrum of a peanut oil sample.

FIG. 5 shows an example of the t2 distribution fingerprint spectrum of a peanut oil sample. The pulse sequence shown in FIG. 2 was used to acquire the two-dimensional relaxation signal of the peanut oil sample. The two-dimensional relaxation signal of peanut oil, $f(\tau_1, n)$, was obtained by fixing $\tau_3$ and changing $\tau_1$ and n, wherein $\tau_1$ is a set of time values, n is cycle number, and $f(\tau_1, n)$ is the signal intensity corresponding to $\tau_1$ and n. The t2 distribution fingerprint spectrum of peanut oil in FIG. 5 was obtained by subtracting the selected reference function F(x, y) from the normalized $f(\tau_1, n)$.

Figure 6:
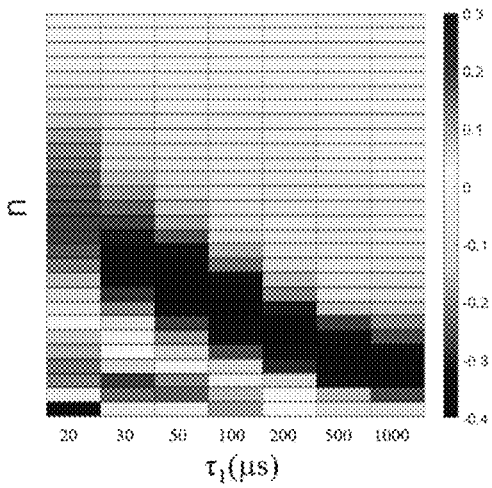
FIG. 6: The t2 distribution fingerprint spectrum of a soybean oil sample.

FIG. 6 shows an example of the t2 distribution fingerprint spectrum of a soybean oil sample. The pulse sequence shown in FIG. 2 was used to acquire the two-dimensional relaxation signal of the soybean oil sample. The two-dimensional relaxation signal of soybean oil, $f(\tau_1, n)$, was obtained by fixing $\tau_3$ and changing $\tau_1$ and n, wherein $\tau_1$ is a set of time values, n is cycle number, and $f(\tau_1, n)$ is the signal intensity corresponding to $\tau_1$ and n. The t2 distribution fingerprint spectrum of soybean oil in FIG. 6 was obtained by subtracting the selected reference function F(x, y) from the normalized $f(\tau_1, n)$.

Figure 7:
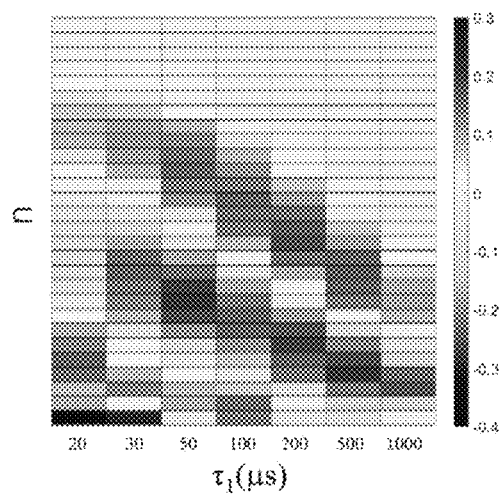
FIG. 7: The t2 distribution fingerprint spectrum of a linseed oil sample.

FIG. 7 shows an example of the t2 distribution fingerprint spectrum of a linseed oil sample. The pulse sequence shown in FIG. 2 was used to acquire the two-dimensional relaxation signal of the linseed oil sample. The two-dimensional relaxation signal of linseed oil, $f(\tau_1, n)$, was obtained by fixing $\tau_3$ and changing $\tau_1$ and n, wherein $\tau_1$ is a set of time values, n is cycle number, and $f(\tau_1, n)$ is the signal intensity corresponding to $\tau_1$ and n. The t2 distribution fingerprint spectrum of linseed oil in FIG. 7 was obtained by subtracting the selected reference function F(x, y) from the normalized $f(\tau_1, n)$.

Figure 8:
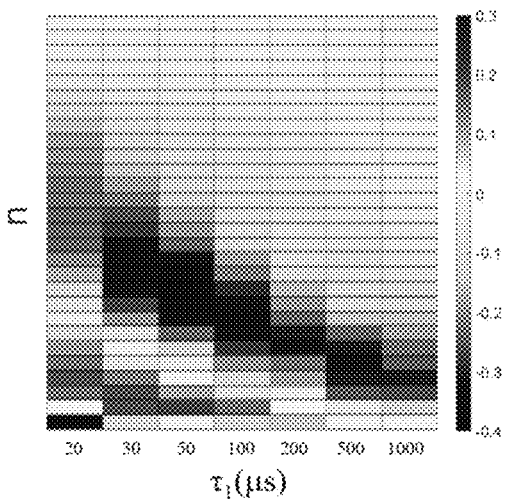
FIG. 8: The t2 distribution fingerprint spectrum of an olive oil sample.

FIG. 8 shows an example of the t2 distribution fingerprint spectrum of an olive oil sample. The pulse sequence shown in FIG. 2 was used to acquire the two-dimensional relaxation signal of the olive oil sample. The two-dimensional relaxation signal of olive oil, $f(\tau_1, n)$, was obtained by fixing $\tau_3$ and changing $\tau_1$ and n, wherein $\tau_1$ is a set of time values, n is cycle number, and $f(\tau_1, n)$ is the signal intensity corresponding to $\tau_1$ and n. The t2 distribution fingerprint spectrum of olive oil in FIG. 8 was obtained by subtracting the selected reference function F(x, y) from the normalized $f(\tau_1, n)$.

Figure 9:
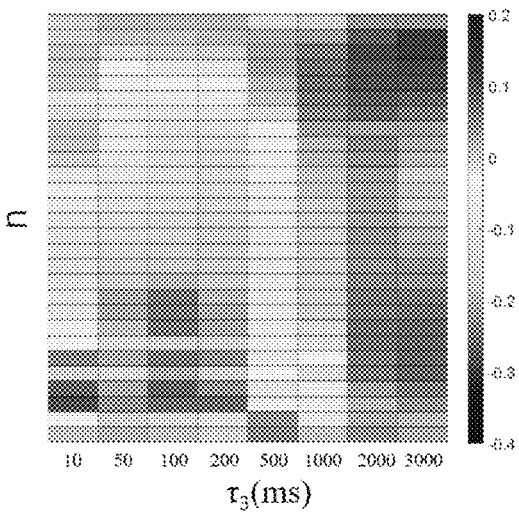
FIG. 9: The t1-t2 correlation fingerprint spectrum of a corn germ oil sample.

FIG. 9 shows an example of the t1-t2 correlation fingerprint spectrum of a corn germ oil sample. The pulse sequence shown in FIG. 2 was used to acquire the two-dimensional relaxation signal of the corn germ oil sample. The two-dimensional relaxation signal of corn germ oil, $f_a(\tau_3, n)$, was obtained by fixing $\tau_1$ and changing $\tau_3$ and n, wherein $\tau_3$ is a set of time values, n is cycle number, and $f_a(\tau_3, n)$ is the signal intensity corresponding to $\tau_3$ and n. The reference function $F_a(x, y)$ is obtained by performing surface fitting of $f_a(\tau_3, n)$. The t1-t2 correlation fingerprint spectrum of corn germ oil in FIG. 9 was obtained by subtracting the selected reference function $F_a(x, y)$ from the normalized $f_a(\tau_3, n)$.

Figure 10:
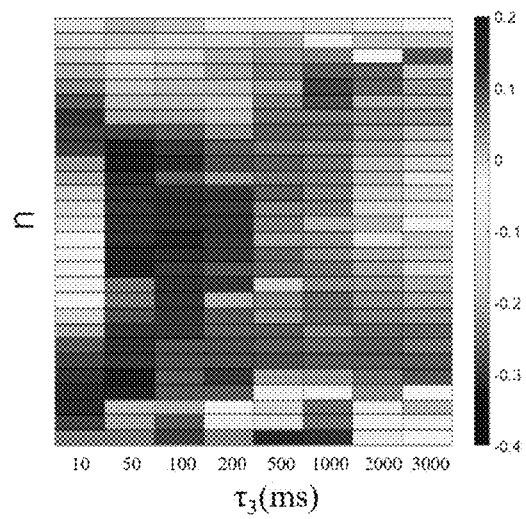
FIG. 10: The t1-t2 correlation fingerprint spectrum of a peanut oil sample.

FIG. 10 shows an example of the $t_1$-$t_2$ correlation fingerprint spectrum of a peanut oil sample. The pulse sequence shown in FIG. 2 was used to acquire the two-dimensional relaxation signal of the peanut oil sample. The two-dimensional relaxation signal of peanut oil, $f_a(\tau_3, n)$, was obtained by fixing $\tau_1$ and changing $\tau_3$ and n, wherein $\tau_3$ is a set of time values, n is cycle number, and $f_a(\tau_3, n)$ is the signal intensity corresponding to $\tau_3$ and n. The $t_1$-$t_2$ correlation fingerprint spectrum of peanut oil in FIG. 10 was obtained by subtracting the selected reference function $F_a(x, y)$ from the normalized $f_a(\tau_3, n)$.

Figure 11:
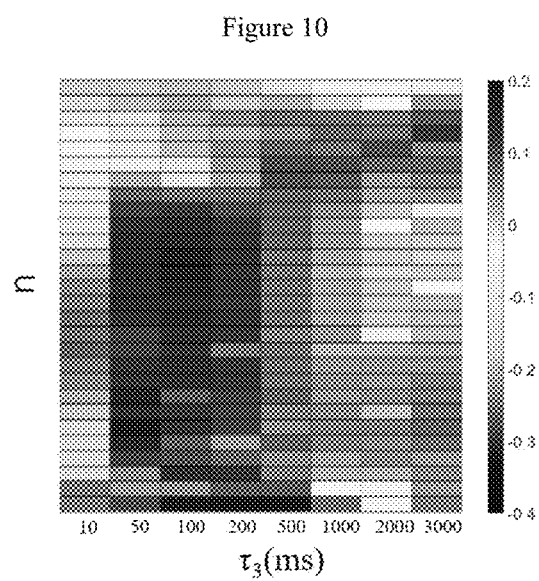
FIG. 11: The t1-t2 correlation fingerprint spectrum of a soybean oil sample.

FIG. 11 shows an example of the $t_1$-$t_2$ correlation fingerprint spectrum of a soybean oil sample. The pulse sequence shown in FIG. 2 was used to acquire the two-dimensional relaxation signal of the soybean oil sample. The two-dimensional relaxation signal of soybean oil, $f_a(\tau_3, n)$, was obtained by fixing $\tau_1$ and changing $\tau_3$ and n, wherein $\tau_3$ is a set of time values, n is cycle number, and $f_a(\tau_3, n)$ is the signal intensity corresponding to $\tau_3$ and n. The $t_1$-$t_2$ correlation fingerprint spectrum of soybean oil in FIG. 11 was obtained by subtracting the selected reference function $F_a(x, y)$ from the normalized $f_a(\tau_3, n)$.

Figure 12:
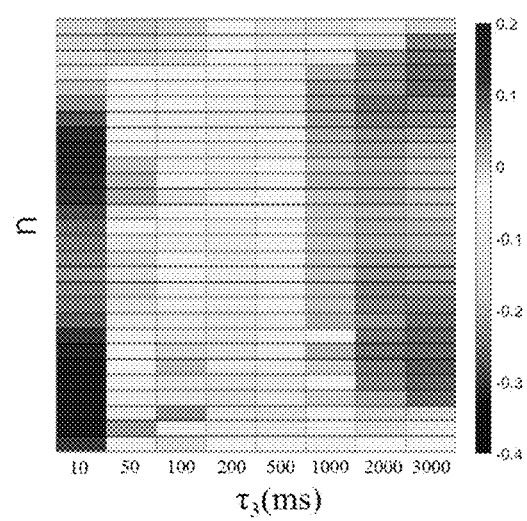
FIG. 12: The t1-t2 correlation fingerprint spectrum of a linseed oil sample.

FIG. 12 shows an example of the $t_1$-$t_2$ correlation fingerprint spectrum of a linseed oil sample. The pulse sequence shown in FIG. 2 was used to acquire the two-dimensional relaxation signal of the linseed oil sample. The two-dimensional relaxation signal of linseed oil, $f_a(\tau_3, n)$, was obtained by fixing T and changing $\tau_3$ and n, wherein $\tau_3$ is a set of time values, n is cycle number, and $f_a(\tau_3, n)$ is the signal intensity corresponding to $\tau_3$ and n. The $\tau_1$-$\tau_2$ correlation fingerprint spectrum of linseed oil in FIG. 12 was obtained by subtracting the selected reference function $F_a(x, y)$ from the normalized $f_a(\tau_3, n)$.

Figure 13:
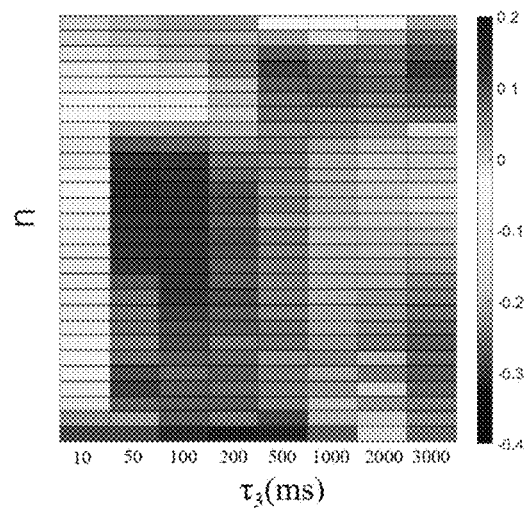
FIG. 13: The t1-t2 correlation fingerprint spectrum of an olive oil sample.

FIG. 13 shows an example of the $t_1$-$t_2$ correlation fingerprint spectrum of an olive oil sample. The pulse sequence shown in FIG. 2 was used to acquire the two-dimensional relaxation signal of the olive oil sample. The two-dimensional relaxation signal of olive oil, $f_a(\tau_3, n)$, was obtained by fixing $\tau_1$ and changing $\tau_3$ and n, wherein $\tau_3$ is a set of time values, n is cycle number, and $f_a(\tau_3, n)$ is the signal intensity corresponding to $\tau_3$ and n. The $t_1$-$t_2$ correlation fingerprint spectrum of olive oil in FIG. 13 was obtained by subtracting the selected reference function $F_a(x, y)$ from the normalized $f_a(\tau_3, n)$.

Figure 14:
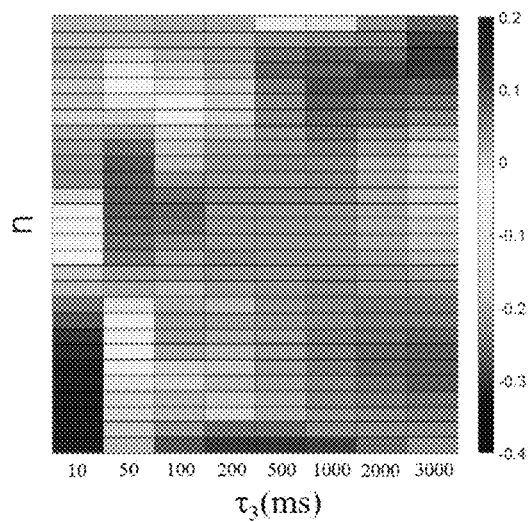
FIG. 14: The t1-t2 correlation fingerprint spectrum of a corn germ oil sample mixed with 1% water by weight.

FIG. 14 shows an example of the $t_1$-$t_2$ correlation fingerprint spectrum of a corn germ oil sample mixed with 1% water by weight. The pulse sequence shown in FIG. 2 was used to acquire the two-dimensional relaxation signal of the corn germ oil sample mixed with 1% water by weight. The two-dimensional relaxation signal of the corn germ oil sample mixed with 1% water by weight, $f_a(\tau_3, n)$, was obtained by fixing $\tau_1$ and changing $\tau_3$ and n, wherein $\tau_3$ is a set of time values, n is cycle number, and $f_a(\tau_3, n)$ is the signal intensity corresponding to $\tau_3$ and n. The $t_1$-$t_2$ correlation fingerprint spectrum of the corn germ oil sample mixed with 1% water by weight in FIG. 14 was obtained by subtracting the selected reference function $F_a(x, y)$ from the normalized $f_a(\tau_3, n)$.

Figure 15:
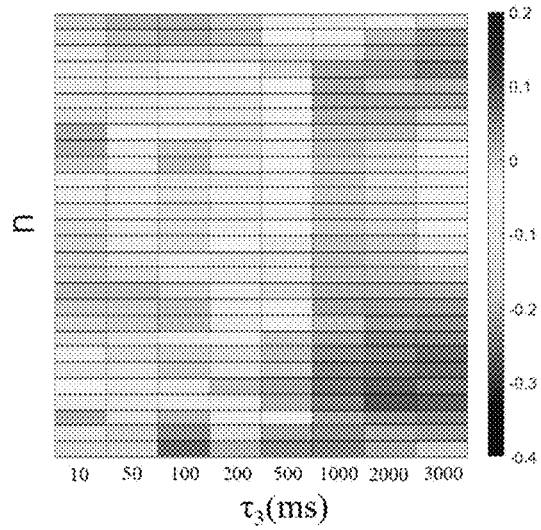
FIG. 15: The t1-t2 correlation fingerprint spectrum of a corn germ oil sample mixed with 1% lard by weight.

FIG. 15 shows an example of the $t_1$-$t_2$ correlation fingerprint spectrum of a corn germ oil sample mixed with 1% lard by weight. The pulse sequence shown in FIG. 2 was used to acquire the two-dimensional relaxation signal of the corn germ oil sample mixed with 1% lard by weight. The two-dimensional relaxation signal of the corn germ oil sample mixed with 1% lard by weight, $f_a(\tau_3, n)$, was obtained by fixing $\tau_1$ and changing $\tau_3$ and n, wherein $\tau_3$ is a set of time values, n is cycle number, and $f_a(\tau_3, n)$ is the signal intensity corresponding to $\tau_3$ and n. The $t_1$-$t_2$ correlation fingerprint spectrum of the corn germ oil sample mixed with 1% lard by weight in FIG. 15 was obtained by subtracting the selected reference function $F_a(x, y)$ from the normalized $f_a(\tau_3, n)$.

Figure 16:
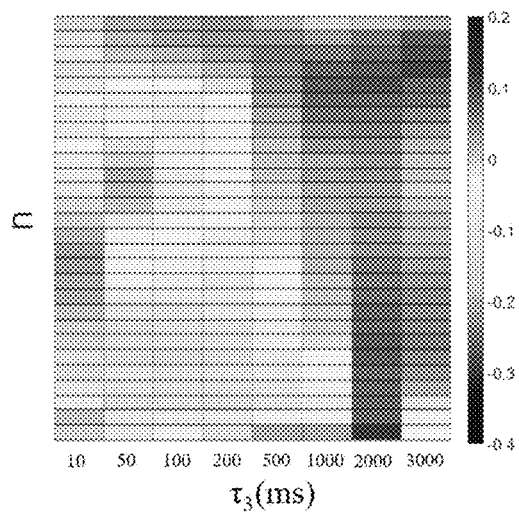
FIG. 16: The t1-t2 correlation fingerprint spectrum of a corn germ oil sample mixed with 1% beef tallow by weight.

FIG. 16 shows an example of the $t_1$-$t_2$ correlation fingerprint spectrum of a corn germ oil sample mixed with 1% beef tallow by weight. The pulse sequence shown in FIG. 2 was used to acquire the two-dimensional relaxation signal of the corn germ oil sample mixed with 1% beef tallow by weight. The two-dimensional relaxation signal of the corn germ oil sample mixed with 1% beef tallow by weight, $f_a(\tau_3, n)$, was obtained by fixing $\tau_1$ and changing $\tau_3$ and n, wherein $\tau_3$ is a set of time values, n is cycle number, and $f_a(\tau_3, n)$ is the signal intensity corresponding to $\tau_3$ and n. The $t_1$-$t_2$ correlation fingerprint spectrum of the corn germ oil sample mixed with 1% beef tallow by weight in FIG. 16 was obtained by subtracting the selected reference function $F_a(x, y)$ from the normalized $f_a(\tau_3, n)$.

Figure 17:
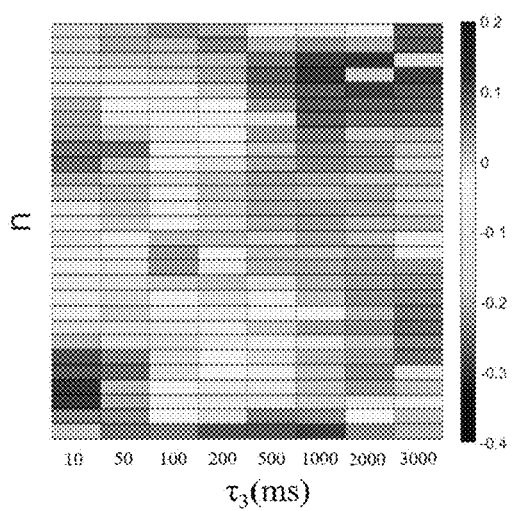
FIG. 17: The t1-t2 correlation fingerprint spectrum of a corn germ oil sample mixed with 1% butter by weight.

FIG. 17 shows an example of the $t_1$-$t_2$ correlation fingerprint spectrum of a corn germ oil sample mixed with 1% butter by weight. The pulse sequence shown in FIG. 2 was used to acquire the two-dimensional relaxation signal of the corn germ oil sample mixed with 1% butter by weight. The two-dimensional relaxation signal of the corn germ oil sample mixed with 1% butter by weight, $f_a(\tau_3, n)$, was obtained by fixing $\tau_1$ and changing $\tau_3$ and n, wherein $\tau_3$ is a set of time values, n is cycle number, and $f_a(\tau_3, n)$ is the signal intensity corresponding to $\tau_3$ and n. The $t_1$-$t_2$ correlation fingerprint spectrum of the corn germ oil sample mixed with 1% butter by weight in FIG. 17 was obtained by subtracting the selected reference function $F_a(x, y)$ from the normalized $f_a(\tau_3, n)$.

Figure 18:
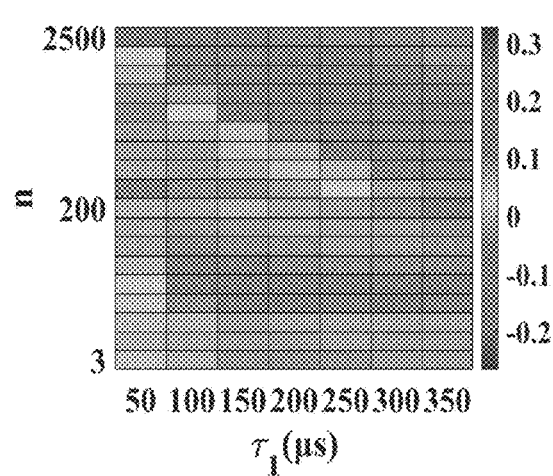
FIG. 18: The t2 distribution fingerprint spectrum of the commercially available cow milk 1.

FIG. 18 shows an example of the t2 distribution fingerprint spectrum of the commercially available cow milk 1. The pulse sequence shown in FIG. 2 was used to acquire the two-dimensional relaxation signal of the commercially available cow milk 1. The two-dimensional relaxation signal of the commercially available cow milk 1, $f(\tau_1, n)$, was obtained by fixing $\tau_3$ and changing $\tau_1$ and n, wherein $\tau_1$ is a set of time values, n is cycle number, and $f(\tau_1, n)$ is the signal intensity corresponding to $\tau_1$ and n. The t2 distribution fingerprint spectrum of the commercially available cow milk 1 in FIG. 18 was obtained by subtracting the selected reference function $F(x, y)$ from the normalized $f(\tau_1, n)$.

Figure 19:
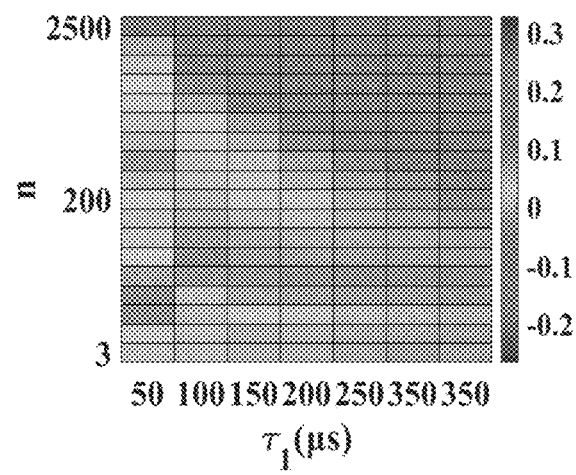
FIG. 19: The t2 distribution fingerprint spectrum of the commercially available cow milk 2.

FIG. 19 shows an example of the t2 distribution fingerprint spectrum of the commercially available cow milk 2. The pulse sequence shown in FIG. 2 was used to acquire the two-dimensional relaxation signal of the commercially available cow milk 2. The two-dimensional relaxation signal of the commercially available cow milk 2, $f(\tau_1, n)$, was obtained by fixing $\tau_3$ and changing $\tau_1$ and n, wherein $\tau_1$ is a set of time values, n is cycle number, and $f(\tau_1, n)$ is the signal intensity corresponding to $\tau_1$ and n. The t2 distribution fingerprint spectrum of the commercially available cow milk 2 in FIG. 19 was obtained by subtracting the selected reference function $F(x, y)$ from the normalized $f(\tau_1, n)$.

Figure 20:
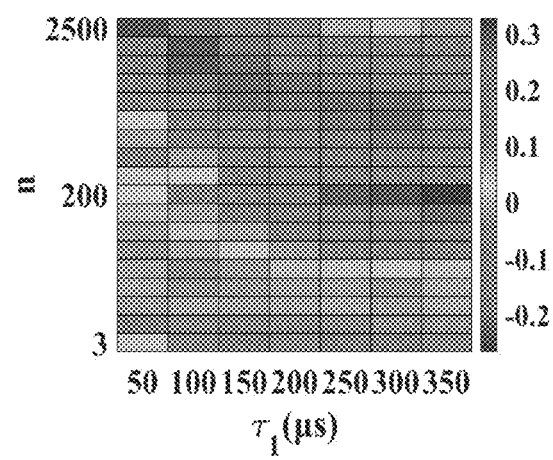
FIG. 20: The t2 distribution fingerprint spectrum of the commercially available goat milk.

FIG. 20 shows an example of the t2 distribution fingerprint spectrum of the commercially available goat milk. The pulse sequence shown in FIG. 2 was used to acquire the two-dimensional relaxation signal of the commercially available goat milk. The two-dimensional relaxation signal of the commercially available goat milk, $f(\tau_1, n)$, was obtained by fixing $\tau_3$ and changing $\tau_1$ and n, wherein $\tau_1$ is a set of time values, n is cycle number, and $f(\tau_1, n)$ is the signal intensity corresponding to $\tau_1$ and n. The $\tau_2$ distribution fingerprint spectrum of the commercially available goat milk in FIG. 20 was obtained by subtracting the selected reference function $F(x, y)$ from the normalized $f(\tau_1, n)$.

Figure 21:
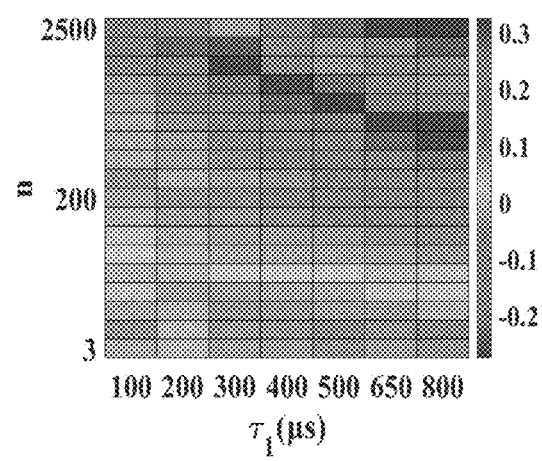
FIG. 21: The t2 distribution fingerprint spectrum of a pig hide gelatin sample.

FIG. 21 shows an example of the t2 distribution fingerprint spectrum of the pig hide gelatin sample. The pulse sequence shown in FIG. 2 was used to acquire the two-dimensional relaxation signal of the pig hide gelatin sample. The two-dimensional relaxation signal of the pig hide gelatin sample, $f(\tau_1, n)$, was obtained by fixing $\tau_3$ and changing $\tau_1$ and n, wherein $\tau_1$ is a set of time values, n is cycle number, and $f(\tau_1, n)$ is the signal intensity corresponding to $\tau_1$ and n. The t2 distribution fingerprint spectrum of the pig hide gelatin sample in FIG. 21 was obtained by subtracting the selected reference function $F(x, y)$ from the normalized $f(\tau_1, n)$.

Figure 22:
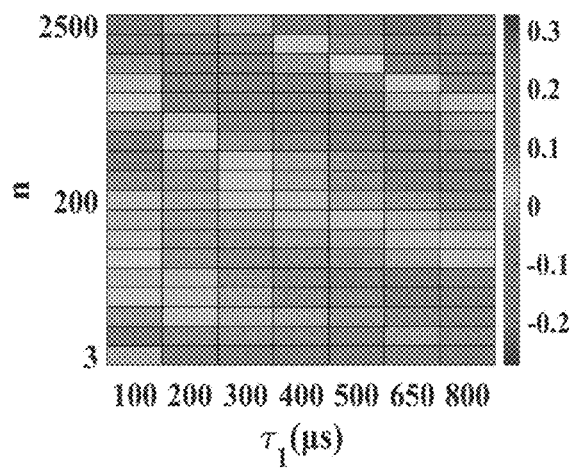
FIG. 22: The t2 distribution fingerprint spectrum of a cow hide gelatin sample.

FIG. 22 shows an example of the t2 distribution fingerprint spectrum of the cow hide gelatin sample. The pulse sequence shown in FIG. 2 was used to acquire the two-dimensional relaxation signal of the cow hide gelatin sample. The two-dimensional relaxation signal of the cow hide gelatin sample, $f(\tau_1, n)$, was obtained by fixing $\tau_3$ and changing $\tau_1$ and n, wherein $\tau_1$ is a set of time values, n is cycle number, and $f(\tau_1, n)$ is the signal intensity corresponding to $\tau_1$ and n. The t2 distribution fingerprint spectrum of the cow hide gelatin sample in FIG. 22 was obtained by subtracting the selected reference function $F(x, y)$ from the normalized $f(\tau_1, n)$.

Figure 23:
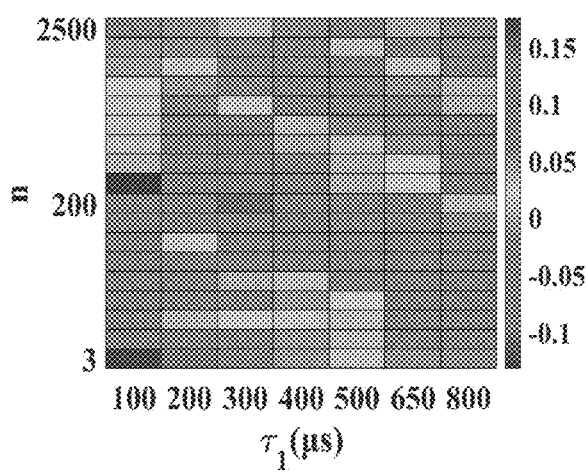
FIG. 23: The t2 distribution fingerprint spectrum of Liaoning scorpion powder solution.

FIG. 23 shows an example of the t2 distribution fingerprint spectrum of Liaoning scorpion powder solution. The pulse sequence shown in FIG. 2 was used to acquire the two-dimensional relaxation signal of Liaoning scorpion powder solution. The two-dimensional relaxation signal of Liaoning scorpion powder solution, $f(\tau_1, n)$, was obtained by fixing $\tau_3$ and changing $\tau_1$ and n, wherein $\tau_1$ is a set of time values, n is cycle number, and $f(\tau_1, n)$ is the signal intensity corresponding to $\tau_1$ and n. The $\tau_2$ distribution fingerprint spectrum of Liaoning scorpion powder solution in FIG. 23 was obtained by subtracting the selected reference function $F(x, y)$ from the normalized $f(\tau_1, n)$.

Figure 24:
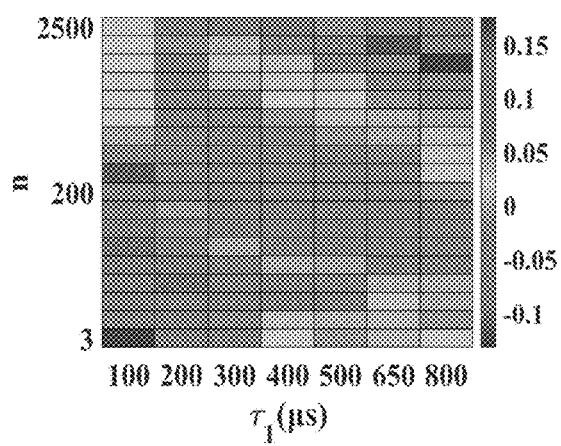
FIG. 24: The t2 distribution fingerprint spectrum of Shanxi scorpion powder solution.

FIG. 24 shows an example of the t2 distribution fingerprint spectrum of Shanxi scorpion powder solution. The pulse sequence shown in FIG. 2 was used to acquire the two-dimensional relaxation signal of Shanxi scorpion powder solution. The two-dimensional relaxation signal of Shanxi scorpion powder solution, $f(\tau_1, n)$, was obtained by fixing $\tau_3$ and changing $\tau_1$ and n, wherein $\tau_1$ is a set of time values, n is cycle number, and $f(\tau_1, n)$ is the signal intensity corresponding to $\tau_1$ and n. The $\tau_2$ distribution fingerprint spectrum of Shanxi scorpion powder solution in FIG. 24 was obtained by subtracting the selected reference function $F(x, y)$ from the normalized $f(\tau_1, n)$.

There is some sample preparation processes in the examples. The methods and steps of the sample preparation processes are well-known in the field.

Example 1—the t2 Distribution Fingerprint Spectrum of a Corn Germ Oil

Sample: a commercially available corn germ oil.
NMR Instrument: Bruker AVANCE III 500 NMR spectrometer. The experimental temperature is room temperature.

Method: The pulse sequence used in this experiment is shown in FIG. 2. In the experiment, $\tau_1$ was set to 20 μs, 30 μs, 50 μs, 100 μs, 200 μs, 500 μs and 1 ms, $\tau_2$ was set to 20 μs and $\tau_3$ was set to 2 ms. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. Thus the two-dimensional relaxation surface $f(\tau_1, n)$ of the corn germ oil was obtained, which then was normalized to $f_n(\tau_1, n)$.

In this example, the reference surface function was obtained by fitting and normalizing two-dimensional relaxation surface $f_n(\tau_1, n)$ of corn germ oil. The reference surface function is:

$$F(x,y) = 18.54 - 17.11 \cdot x - 6.667 \cdot y + 6.41 \cdot x^2 + 4.15 \cdot x \cdot y + 0.3606 \cdot y^2 - 1.232 \cdot x^3 - 1.024 \cdot x^2 \cdot y - 0.08823 \cdot x \cdot y^2 + 0.04467 \cdot y^3 + 0.1212 \cdot x^4 40.1138 \cdot x^3 \cdot y + 0.02533 \cdot x^2 \cdot y^2 - 0.02851 \cdot x \cdot y^3 + 0.003422 \cdot y^4 - 0.00484 \cdot x^5 - 0.004637 \cdot x^4 \cdot y - 0.002608 \cdot x^3 \cdot y^2 + 0.001928 \cdot x^2 \cdot y^3 + 0.001074 \cdot x \cdot y^4 + 0.0000372 \cdot y^5$$

The t2 distribution fingerprint spectrum of the corn germ oil (FIG. 4) can be obtained by subtracting the reference surface $F(x,y)$ from $f_n(\tau_1, n)$.

Example 2—the t2 Distribution Fingerprint Spectrum of a Peanut Oil

Sample: a commercially available peanut oil.
NMR Instrument: Bruker AVANCE III 500 NMR spectrometer. The experimental temperature is room temperature.

Method: The pulse sequence used in this experiment is shown in FIG. 2. In the experiment, $\tau_1$ was set to 20 μs, 30 μs, 50 μs, 100 μs, 200 μs, 500 μs and 1 ms, $\tau_2$ was set to 20 μs and $\tau_3$ was set to 2 ms. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f(\tau_1, n)$ of the peanut oil was obtained, which then was normalized to $f_n(\tau_1, n)$. In this example, the reference surface function was that of the peanut oil:

$$F(x,y) = 18.54 - 17.11 \cdot x - 6.667 \cdot y + 6.41 \cdot x^2 + 4.15 \cdot x \cdot y + 0.3606 \cdot y^2 - 1.232 \cdot x^3 - 1.024 \cdot x^2 \cdot y - 0.08823 \cdot x \cdot y^2 + 0.04467 \cdot y^3 + 0.1212 \cdot x^4 + 0.1138 \cdot x^3 \cdot y + 0.02533 \cdot x^2 \cdot y^2 - 0.02851 \cdot x \cdot y^3 + 0.003422 \cdot y^4 - 0.00484 \cdot x^3 - 0.004637 \cdot x^4 \cdot y - 0.002608 \cdot x^3 \cdot y^2 + 0.001928 \cdot x^2 \cdot y^3 + 0.001074 \cdot x \cdot y^4 + 0.0000372 \cdot y^5$$

The t2 distribution fingerprint spectrum of the peanut oil (FIG. 5) can be obtained by subtracting the reference surface $F(x,y)$ from $f_n(\tau_1, n)$.

Example 3—the t2 Distribution Fingerprint Spectrum of a Soybean Oil

Sample: a commercially available soybean oil
NMR Instrument: Bruker AVANCE III 500 NMR spectrometer. The experimental temperature is room temperature.

Method: The pulse sequence used in this experiment is shown in FIG. 2. In the experiment, $\tau_1$ was set to 20μ, 30μ, 50μ, 100 μs, 200 μs, 500 μs and 1 ms, $\tau_2$ was set to 20 μs and $\tau_3$ was set to 2 ms. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f(\tau_1, n)$ of the soybean oil was obtained, which then was normalized to $f_n(\tau_1, n)$. In this example, the reference surface function was that of the corn germ oil:

$$F(x,y) = 18.54 - 17.11 \cdot x - 6.667 \cdot y + 6.41 \cdot x^2 + 4.15 \cdot x \cdot y + 0.3606 \cdot y^2 - 1.232 \cdot x^3 - 1.024 \cdot x^2 \cdot y - 0.08823 \cdot x \cdot y^2 + 0.04467 \cdot y^3 + 0.1212 \cdot x^4 + 0.1138 \cdot x^3 \cdot y + 0.02533 \cdot x^2 \cdot y^2 - 0.02851 \cdot x \cdot y^3 + 0.003422 \cdot y^4 - 0.00484 \cdot x^5 - 0.004637 \cdot x^4 \cdot y - 0.002608 \cdot x^3 \cdot y^2 + 0.001928 - x^2 \cdot y^3 + 0.001074 \cdot x - y^4 + 0.0000372 \cdot y^5$$

The t2 distribution fingerprint spectrum of the soybean oil (FIG. 6) can be obtained by subtracting the reference surface $F(x,y)$ from $f_n(\tau_1, n)$.

Example 4—the t2 Distribution Fingerprint Spectrum of a Linseed Oil

Sample: a commercially available linseed oil.
NMR Instrument: Bruker AVANCE III 500 NMR spectrometer. The experimental temperature is room temperature.

Method: The pulse sequence used in this experiment is shown in FIG. 2. In the experiment, $\tau_1$ was set to 20 μs, 30

μs, 50 μs, 100 μs, 200 μs, 500 μs and 1 ms, $\tau_2$ was set to 20 μs and $\tau_3$ was set to 2 ms. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f(\tau_1, n)$ of the linseed oil was obtained, which then was normalized to $f_n(\tau_1, n)$.

In this example, the reference surface function was that of the corn germ oil:

$$F(x,y)=18.54-17.11 \cdot x-6.667 \cdot y+6.41 \cdot x^2+4.15 \cdot x \cdot y+\\0.3606 \cdot y^2-1.232 \cdot x^3-1.024 \cdot x^2 \cdot y-0.08823 \cdot x \cdot y^2+\\0.04467 \cdot y^3+0.1212 \cdot x^4+0.1138 \cdot x^3 \cdot y+\\0.02533 \cdot x^2 \cdot y^2-0.02851 \cdot x \cdot y^3+0.003422 \cdot y^4-\\0.00484 \cdot x^5-0.004637 \cdot x^4 \cdot y-0.002608 \cdot x^3 \cdot y^2+\\0.001928 \cdot x^2 \cdot y^3+0.001074 \cdot x \cdot y^4+0.0000372 \cdot y^5$$

The t2 distribution fingerprint spectrum of the linseed oil (FIG. 7) can be obtained by subtracting the reference surface $F(x,y)$ from $f_n(\tau_1, n)$.

Example 5—the t2 Distribution Fingerprint Spectrum of an Olive Oil

Sample: a commercially available olive oil.

NMR Instrument: Bruker AVANCE III 500 NMR spectrometer. The experimental temperature is room temperature.

Method: The pulse sequence used in this experiment is shown in FIG. 2. In the experiment, $\tau_1$ was set to 20 μs, 30 μs, 50 μs, 100 μs, 200 μs, 500 μs and 1 ms, $\tau_2$ was set to 20 μs and $\tau_3$ was set to 2 ms. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f(\tau_1, n)$ of the olive oil was obtained, which then was normalized to $f_n(\tau_1, n)$.

In this example, the reference surface function was that of the corn germ oil:

$$F(x,y)=18.54-17.11 \cdot x-6.667 \cdot y+6.41 \cdot x^2+4.15 \cdot x \cdot y+\\0.3606 \cdot y^2-1.232 \cdot x^3-1.024 \cdot x^2 \cdot y-0.08823 \cdot x \cdot y^2+\\0.04467 \cdot y^3+0.1212 \cdot x^4+0.1138 \cdot x^3 \cdot y+\\0.02533 \cdot x^2 \cdot y^2-0.02851 \cdot x \cdot y^3+0.003422 \cdot y^4-\\0.00484 \cdot x^5-0.004637 \cdot x^4 \cdot y-0.002608 \cdot x^3 \cdot y^2+\\0.001928 \cdot x^2 \cdot y^3+0.001074 \cdot x \cdot y^4+0.0000372 \cdot y^5$$

The t2 distribution fingerprint spectrum of the olive oil (FIG. 8) can be obtained by subtracting the reference surface $F(x,y)$ from $f_n(\tau_1, n)$.

Example 6—the $t_1$-$t_2$ Correlation Fingerprint Spectrum of a Corn Germ Oil Sample: a commercially available corn germ oil.

NMR Instrument: Bruker AVANCE III 500 NMR spectrometer. The experimental temperature is room temperature.

Method: The pulse sequence used in this experiment is shown in FIG. 2. In the experiment, $\tau_1$ was set to 20 μs, $\tau_2$ was set to 20 μs and $\tau_3$ was set to 10 ms, 50 ms, 100 ms, 200 ms, 500 ms and 1 s, 2 s and 3 s. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f_a(\tau_3, n)$ of the corn germ oil was obtained, which then was normalized to $f_n(\tau_3, n)$.

In this example, the reference surface function was obtained by fitting and normalizing the two-dimensional relaxation surface $f_n(\tau_3, n)$ of the corn germ oil. The reference surface function is:

$$F_a(x,y)=-2.281+2.317 \cdot x-0.4775 \cdot y-0.9071 \cdot x^2-\\0.001151 \cdot x \cdot y+0.2854 \cdot y^2+0.1461 \cdot x^3+\\0.09387 \cdot x^2 \cdot y-0.1417 \cdot x \cdot y^2-0.007143 \cdot y^3-0.00962-\\x^4-0.01736 \cdot x^3 \cdot y+0.01505 \cdot x^2 \cdot y^2+0.00902 \cdot x \cdot y^3-\\0.002398 \cdot y^4+0.0001928 \cdot x^5+0.0008389 \cdot x^4 \cdot y-\\0.0003571 \cdot x^3 \cdot y^2-0.0006947 \cdot x^2 \cdot y^3+\\0.000005745 \cdot x \cdot y^4+0.00008974 \cdot y^5$$

The $t_1$-$t_2$ correlation fingerprint spectrum of the corn germ oil (FIG. 9) can be obtained by subtracting the reference surface $F_a(x,y)$ from $f_n(\tau_3, n)$.

Example 7—the $t_1$-$t_2$ Correlation Fingerprint Spectrum of a Peanut Oil

Sample: a commercially available peanut oil.

NMR Instrument: Bruker AVANCE III 500 NMR spectrometer. The experimental temperature is room temperature.

Method: The pulse sequence used in this experiment is shown in FIG. 2. In the experiment, $\tau_1$ was set to 20 μs, $\tau_2$ was set to 20 μs and $\tau_3$ was set to 10 ms, 50 ms, 100 ms, 200 ms, 500 ms and 1 s, 2 s and 3 s. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f_a(\tau_3, n)$ of the peanut oil was obtained, which then was normalized to $f_n(\tau_3, n)$.

In this example, the reference surface function was that of the corn germ oil:

$$F_a(x,y)=-2.281+2.317 \cdot x-0.4775 \cdot y-0.9071 \cdot x^2-\\0.001151 \cdot x \cdot y+0.2854 \cdot y^2+0.1461 \cdot x^3+\\0.09387 \cdot x^2 \cdot y-0.1417 \cdot x \cdot y^2-0.007143 \cdot y^3-0.00962-\\x^4-0.01736 \cdot x^3 \cdot y+0.01505 \cdot x^2 \cdot y^2+0.00902 \cdot x \cdot y^3-\\0.002398 \cdot y^4+0.0001928 \cdot x^3+0.0008389 \cdot x^4 \cdot y-\\0.0003571 \cdot x^3 \cdot y^2-0.0006947 \cdot x^2 \cdot y^3+\\0.000005745 \cdot x \cdot y^4+0.00008974 \cdot y^5$$

The $t_1$-$t_2$ correlation fingerprint spectrum of the peanut oil (FIG. 10) can be obtained by subtracting the reference surface $F_a(x,y)$ from $f_n(\tau_3, n)$.

Example 8—the $t_1$-$t_2$ Correlation Fingerprint Spectrum of a Soybean Oil

Sample: a commercially available soybean oil.

NMR Instrument: Bruker AVANCE III 500 NMR spectrometer. The experimental temperature is room temperature.

Method: The pulse sequence used in this experiment is shown in FIG. 2. In the experiment, $\tau_1$ was set to 20 μs, $\tau_2$ was set to 20 μs and $\tau_3$ was set to 10 ms, 50 ms, 100 ms, 200 ms, 500 ms and 1 s, 2 s and 3 s. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f_a(\tau_3, n)$ of the soybean oil was obtained, which then was normalized to $f_n(\tau_3, n)$.

In this example, the reference surface function was that of corn germ oil:

$$F_a(x,y)=-2.281+2.317 \cdot x-0.4775 \cdot y-0.9071 \cdot x^2-\\0.001151 \cdot x \cdot y+0.2854 \cdot y^2+0.1461 \cdot x^3+\\0.09387 \cdot x^2 \cdot y-0.1417 \cdot x \cdot y^2-0.007143 \cdot y^3-\\0.00962 \cdot x^4-0.01736 \cdot x^3 \cdot y+0.01505 \cdot x^2 \cdot y^2+\\0.00902 \cdot x \cdot y^3-0.002398 \cdot y^4+0.0001928 \cdot x^5+\\0.0008389 \cdot x^4 \cdot y-0.0003571 \cdot x^3 \cdot y^2-\\0.0006947 \cdot x^2 \cdot y^3+0.000005745 \cdot x \cdot y^4+\\0.00008974 \cdot y^5$$

The $t_1$-$t_2$ correlation fingerprint spectrum of the soybean oil (FIG. 11) can be obtained by subtracting the reference surface $F_a(x,y)$ from $f_n(\tau_3, n)$.

Example 9—the $t_1$-$t_2$ Correlation Fingerprint Spectrum of a Linseed Oil

Sample: a commercially available linseed oil.
NMR Instrument: Bruker AVANCE III 500 NMR spectrometer. The experimental temperature is room temperature.
Method: The pulse sequence used in this experiment is shown in FIG. 2. In the experiment, $\tau_1$ was set to 20 μs, $\tau_2$ was set to 20 μs and $\tau_3$ was set to 10 ms, 50 ms, 100 ms, 200 ms, 500 ms and 1 s, 2 s and 3 s. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f_a(\tau_3, n)$ of the linseed oil was obtained, which then was normalized to $f_n(\tau_3, n)$.
In this example, the reference surface function was that of the corn germ oil:

$$F_a(x,y) = -2.281 + 2.317 \cdot x - 0.4775 \cdot y - 0.9071 \cdot x^2 - 0.001151 \cdot x \cdot y + 0.2854 \cdot y^2 + 0.1461 \cdot x^3 + 0.09387 \cdot x^2 \cdot y - 0.1417 \cdot x \cdot y^2 - 0.007143 \cdot y^3 - 0.00962 \cdot x^4 - 0.01736 \cdot x^3 \cdot y + 0.01505 \cdot x^2 \cdot y^2 + 0.00902 \cdot x \cdot y^3 - 0.002398 \cdot y^4 + 0.0001928 \cdot x^5 + 0.0008389 \cdot x^4 \cdot y - 0.0003571 \cdot x^3 \cdot y^2 - 0.0006947 \cdot x^2 \cdot y^3 + 0.000005745 \cdot x - y^4 + 0.00008974 \cdot y^5$$

The $t_1$-$t_2$ correlation fingerprint spectrum of the linseed oil (FIG. 12) can be obtained by subtracting the reference surface $F_a(x,y)$ from $f_n(\tau_3, n)$.

Example 10—the $t_1$-$t_2$ Correlation Fingerprint Spectrum of an Olive Oil

Sample: a commercially available olive oil.
NMR Instrument: Bruker AVANCE III 500 NMR spectrometer. The experimental temperature is room temperature.
Method: The pulse sequence used in this experiment is shown in FIG. 2. In the experiment, $\tau_1$ was set to 20 μs, $\tau_2$ was set to 20 μs and $\tau_3$ was set to 10 ms, 50 ms, 100 ms, 200 ms, 500 ms and 1 s, 2 s and 3 s. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f_a(\tau_3, n)$ of the olive oil was obtained, which then was normalized to $f_n(\tau_3, n)$.
In this example, the reference surface function was that of corn germ oil:

$$F_a(x,y) = -2.281 + 2.317 \cdot x - 0.4775 \cdot y - 0.9071 \cdot x^2 - 0.001151 \cdot x \cdot y + 0.2854 \cdot y^2 + 0.1461 \cdot x^3 + 0.09387 \cdot x^2 \cdot y - 0.1417 \cdot x \cdot y^2 - 0.007143 \cdot y^3 - 0.00962 \cdot x^4 - 0.01736 \cdot x^3 \cdot y + 0.01505 \cdot x^2 \cdot y^2 + 0.00902 \cdot x \cdot y^3 - 0.002398 \cdot y^4 + 0.0001928 \cdot x^5 + 0.0008389 \cdot x^4 \cdot y - 0.0003571 \cdot x^3 \cdot y^2 - 0.0006947 \cdot x^2 \cdot y^3 + 0.000005745 \cdot x \cdot y^4 + 0.00008974 \cdot y^5$$

The $t_1$-$t_2$ correlation fingerprint spectrum of the olive oil (FIG. 13) can be obtained by subtracting the reference surface $F_a(x,y)$ from $f_n(\tau_3, n)$.

Example 11—The $t_1$-$t_2$ correlation fingerprint spectrum of a corn germ oil sample mixed with 1% water by weight Sample: a commercially available corn germ oil sample mixed with 1% water by weight.
NMR Instrument: Bruker AVANCE III 500 NMR spectrometer. The experimental temperature is room temperature.
Method: The pulse sequence used in this experiment is shown in FIG. 2. In the experiment, $\tau_1$ was set to 20 μs, $\tau_2$ was set to 20 μs and $\tau_3$ was set to 10 ms, 50 ms, 100 ms, 200 ms, 500 ms and 1 s, 2 s and 3 s. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f_a(\tau_3, n)$ of the corn germ oil was obtained, which then was normalized to $f_n(\tau_3, n)$.
In this example, the reference surface function was that of the corn germ oil:

$$F_a(x,y) = -2.281 + 2.317 \cdot x - 0.4775 \cdot y - 0.9071 \cdot x^2 - 0.001151 \cdot x \cdot y + 0.2854 \cdot y^2 + 0.1461 \cdot x^3 + 0.09387 \cdot x^2 \cdot y - 0.1417 \cdot x \cdot y^2 - 0.007143 \cdot y^3 - 0.00962 \cdot x^4 - 0.01736 \cdot x^3 \cdot y + 0.01505 \cdot x^2 \cdot y^2 + 0.00902 \cdot x \cdot y^3 - 0.002398 \cdot y^4 + 0.0001928 \cdot x^5 + 0.0008389 \cdot x^4 \cdot y - 0.0003571 \cdot x^3 \cdot y^2 - 0.0006947 \cdot x^2 \cdot y^3 + 0.000005745 \cdot x - y^4 + 0.00008974 - y^5$$

The $t_1$-$t_2$ correlation fingerprint spectrum of the corn germ oil sample mixed with 1% water by weight (FIG. 14) can be obtained by subtracting the reference surface $F_a(x,y)$ from $f_n(\tau_3, n)$.

Example 12—the $t_1$-$t_2$ Correlation Fingerprint Spectrum of a Corn Germ Oil Sample Mixed with 1% Lard by Weight Sample: a commercially available corn germ oil sample mixed with 1% lard by weight.
NMR Instrument: Bruker AVANCE III 500 NMR spectrometer. The experimental temperature is room temperature.
Method: The pulse sequence used in this experiment is shown in FIG. 2. In the experiment, $\tau_1$ was set to 20 μs, $\tau_2$ was set to 20 μs and $\tau_3$ was set to 10 ms, 50 ms, 100 ms, 200 ms, 500 ms and 1 s, 2 s and 3 s. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f_a(\tau_3, n)$ of the corn germ oil sample mixed with 1% lard by weight was obtained, which then was normalized to $f_n(\tau_3, n)$.
In this example, the reference surface function was that of the corn germ oil:

$$F_a(x,y) = -2.281 + 2.317 \cdot x - 0.4775 \cdot y - 0.9071 \cdot x^2 - 0.001151 \cdot x \cdot y + 0.2854 \cdot y^2 + 0.1461 \cdot x^3 + 0.09387 \cdot x^2 \cdot y - 0.1417 \cdot x \cdot y^2 - 0.007143 \cdot y^3 - 0.00962 \cdot x^4 - 0.01736 \cdot x^3 \cdot y + 0.01505 \cdot x^2 \cdot y^2 + 0.00902 \cdot x \cdot y^3 - 0.002398 \cdot y^4 + 0.0001928 \cdot x^5 + 0.0008389 \cdot x^4 \cdot y - 0.0003571 \cdot x^3 \cdot y^2 - 0.0006947 \cdot x^2 \cdot y^3 + 0.000005745 \cdot x \cdot y^4 + 0.00008974 \cdot y^5$$

The $t_1$-$t_2$ correlation fingerprint spectrum of the corn germ oil sample mixed with 1% lard by weight (FIG. 15) can be obtained by subtracting the reference surface $F_a(x,y)$ from $f_n(\tau_3, n)$.

Example 13—the $t_1$-$t_2$ Correlation Fingerprint Spectrum of a Corn Germ Oil Sample Mixed with 1% Beef Tallow by Weight Sample: a commercially available corn germ oil sample mixed with 1% beef tallow by weight.

NMR Instrument: Bruker AVANCE III 500 NMR spectrometer. The experimental temperature is room temperature.

Method: The pulse sequence used in this experiment is shown in FIG. 2. In the experiment, $\tau_1$ was set to 20 µs, $\tau_2$ was set to 20 µs and $\tau_3$ was set to 10 ms, 50 ms, 100 ms, 200 ms, 500 ms and 1 s, 2 s and 3 s. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f_a(\tau_3, n)$ of the corn germ oil sample mixed with 1% beef tallow by weight was obtained, which then was normalized to $f_n(\tau_3, n)$.

In this example, the reference surface function was that of the corn germ oil:

$$F_a(x,y) = -2.281 + 2.317 \cdot x - 0.4775 \cdot y - 0.9071 \cdot x^2 - 0.001151 \cdot x \cdot y + 0.2854 \cdot y^2 + 0.1461 \cdot x^3 + 0.09387 \cdot x^2 \cdot y - 0.1417 \cdot x \cdot y^2 - 0.007143 \cdot y^3 - 0.00962 \cdot x^4 - 0.01736 \cdot x^3 \cdot y + 0.01505 \cdot x^2 \cdot y^2 + 0.00902 \cdot x \cdot y^3 - 0.002398 \cdot y^4 + 0.0001928 \cdot x^5 + 0.0008389 \cdot x^4 \cdot y - 0.0003571 \cdot x^3 \cdot y^2 - 0.0006947 \cdot x^2 \cdot y^3 + 0.000005745 \cdot x \cdot y^4 + 0.00008974 \cdot y^5$$

The $t_1$-$t_2$ correlation fingerprint spectrum of the corn germ oil sample mixed with 1% beef tallow by weight (FIG. 16) can be obtained by subtracting the reference surface $F_a(x,y)$ from $f_n(\tau_3, n)$.

Example 14—the $t_1$-$t_2$ Correlation Fingerprint Spectrum of a Corn Germ Oil Sample Mixed with 1% Butter by Weight Sample: a commercially available corn germ oil sample mixed with 1% butter by weight.

NMR Instrument: Bruker AVANCE III 500 NMR spectrometer. The experimental temperature is room temperature.

Method: The pulse sequence used in this experiment is shown in FIG. 2. In the experiment, $\tau_1$ was set to 20 µs, $\tau_2$ was set to 20 µs and $\tau_3$ was set to 10 ms, 50 ms, 100 ms, 200 ms, 500 ms and 1 s, 2 s and 3 s. The number of repetition, n, was set to 1, 2, 5, 10, 15, 20, 30, 50, 80, 100, 150, 200, 300, 400, 500, 700, 900, 1200, 1500, 2000, 3000, 5000, 7000, 10000, 15000, 20000, 30000 and 40000. The two-dimensional relaxation surface $f_a(\tau_3, n)$ of the corn germ oil was obtained, which then was normalized to $f_n(\tau_3, n)$.

In this example, the reference surface function was obtained by fitting the normalized two-dimensional relaxation surface $f_n(\tau_3, n)$ of corn germ oil. The reference surface function is:

$$F_a(x,y) = -2.281 + 2.317 \cdot x - 0.4775 \cdot y - 0.9071 \cdot x^2 - 0.001151 \cdot x \cdot y + 0.2854 \cdot y^2 + 0.1461 \cdot x^3 + 0.09387 \cdot x^2 \cdot y - 0.1417 \cdot x \cdot y^2 - 0.007143 \cdot y^3 - 0.00962 \cdot x^4 - 0.01736 \cdot x^3 \cdot y + 0.01505 \cdot x^2 \cdot y^2 + 0.00902 \cdot x \cdot y^3 - 0.002398 \cdot y^4 + 0.0001928 \cdot x^5 + 0.0008389 \cdot x^4 \cdot y - 0.0003571 \cdot x^3 \cdot y^2 - 0.0006947 \cdot x^2 \cdot y^3 + 0.000005745 \cdot x \cdot y^4 + 0.00008974 \cdot y^5$$

The $t_1$-$t_2$ correlation fingerprint spectrum of the corn germ oil sample mixed with 1% butter by weight (FIG. 17) can be obtained by subtracting the reference surface $F_a(x,y)$ from $f_n(\tau_3, n)$.

Example 15—the t2 Distribution Fingerprint Spectrum of a Commercially Available Cow Milk 1

Sample: a commercially available cow milk 1.

NMR Instrument: VTMR20-010V-I relaxometry, Niumag Corp., Ltd., Shanghai, China. The Bo field is 0.5±0.05 T and the $^1$H Larmor frequency is 21.3 MHz. The experimental temperature is room temperature.

Method: The pulse sequence used in this experiment is shown in FIG. 2. In the experiment, $\tau_1$ was set to 50 µs, 100 µs, 150 µs, 200 µs, 250 µs, 300 µs and 350 µs, $\tau_2$ was set to 20 µs and $\tau_3$ was set to 100 µs. The number of repetition, n, was set to 3, 5, 10, 20, 40, 80, 100, 150, 200, 250, 300, 400, 500, 700, 900, 1200, 1500, and 2500. The two-dimensional relaxation surface $f(\tau_1, n)$ of the commercially available cow milk 1 was obtained, which then was normalized to $f_n(\tau_1, n)$.

In this example, the reference surface function was obtained by fitting and normalizing the average value of two-dimensional relaxation surface $f_n(\tau_1, n)$ of the two commercially available cow milks and the goat milk. The reference surface function is:

$$F(x,y) = -0.4201 - 0.2412 \cdot x - 0.7473 \cdot y - 0.0085 \cdot x^2 - 0.2879 \cdot x \cdot y - 0.4974 \cdot y^2 + 0.0201 \cdot x^3 + 0.0121 \cdot x^2 \cdot y - 0.0027 \cdot x \cdot y^2 + 0.0213 \cdot y^3 - 0.0195 \cdot x^4 - 0.0061 \cdot x^3 \cdot y + 0.0379 \cdot x^2 \cdot y^2 + 0.1243 \cdot x \cdot y^3 + 0.1041 \cdot y^4 - 0.0102 \cdot x^5 - 0.0052 \cdot x^4 \cdot y - 0.0047 \cdot x^3 \cdot y^2 + 0.0137 \cdot x^2 \cdot y^3 + 0.0411 \cdot x \cdot y^4 + 0.0214 \cdot y^5$$

The t2 distribution fingerprint spectrum of the commercially available cow milk 1 (FIG. 18) can be obtained by subtracting the reference surface $F(x,y)$ from $f_n(\tau_1, n)$.

Example 16—the t2 Distribution Fingerprint Spectrum of a Commercially Available Cow Milk 2

Sample: a commercially available cow milk 2.

NMR Instrument: VTMR20-010V-I relaxometry, Niumag Corp., Ltd., Shanghai, China. The Bo field is 0.5±0.05 T and the $^1$H Larmor frequency is 21.3 MHz. The experimental temperature is room temperature.

Method: The pulse sequence used in this experiment is shown in FIG. 2. In the experiment, $\tau_1$ was set to 50 µs, 100 µs, 150 µs, 200 µs, 250 µs, 300 µs and 350 µs, $\tau_2$ was set to 20 µs and $\tau_3$ was set to 100 µs. The number of repetition, n, was set to 3, 5, 10, 20, 40, 80, 100, 150, 200, 250, 300, 400, 500, 700, 900, 1200, 1500, and 2500. The two-dimensional relaxation surface $f(\tau_1, n)$ of the commercially available cow milk 2 was obtained, which then was normalized to $f_n(\tau_1, n)$.

In this example, the reference surface function was obtained by fitting and normalizing the average value of two-dimensional relaxation surface $f_n(\tau_1, n)$ of the two commercially available cow milks and the goat milk. The reference surface function is:

$$F(x,y) = -0.4201 - 0.2412 \cdot x - 0.7473 \cdot y - 0.0085 \cdot x^2 - 0.2879 \cdot x \cdot y - 0.4974 \cdot y^2 + 0.0201 \cdot x^3 + 0.0121 \cdot x^2 \cdot y - 0.0027 \cdot x \cdot y^2 + 0.0213 \cdot y^3 - 0.0195 \cdot x^4 - 0.0061 \cdot x^3 \cdot y + 0.0379 \cdot x^2 \cdot y^2 + 0.1243 \cdot x \cdot y^3 + 0.1041 \cdot y^4 - 0.0102 \cdot x^5 - 0.0052 \cdot x^4 \cdot y - 0.0047 \cdot x^3 \cdot y^2 + 0.0137 \cdot x^2 \cdot y^3 + 0.0411 \cdot x \cdot y^4 + 0.0214 \cdot y^5$$

The t2 distribution fingerprint spectrum of the commercially available cow milk 2 (FIG. 19) can be obtained by subtracting the reference surface $F(x,y)$ from $f_n(1, n)$.

Example 17—the t2 Distribution Fingerprint Spectrum of a Commercially Available Goat Milk Sample: a commercially available goat milk.

NMR Instrument: VTMR20-010V-I relaxometry, Niumag Corp., Ltd., Shanghai, China. The Bo field is 0.5±0.05 T and the $^1$H Larmor frequency is 21.3 MHz. The experimental temperature is room temperature.

Method: The pulse sequence used in this experiment is shown in FIG. 2. In the experiment, $\tau_1$ was set to 50 µs, 100 µs, 150 µs, 200 µs, 250 µs, 300 µs and 350 µs, $\tau_2$ was set to 20 μs and $\tau_3$ was set to 100 μs. The number of repetition, n, was set to 3, 5, 10, 20, 40, 80, 100, 150, 200, 250, 300, 400, 500, 700, 900, 1200, 1500, and 2500. The two-dimensional relaxation surface f($\tau_1$, n) of the commercially available goat milk was obtained, which then was normalized to $f_n(\tau_1, n)$.

In this example, the reference surface function was obtained by fitting and normalizing the average value of two-dimensional relaxation surface $f_n(\tau_1, n)$ of the commercially available cow milks and goat milk. The reference surface function is:

$$F(x,y)=-0.4201-0.2412 \cdot x-0.7473 \cdot y-0.0085 \cdot x^2-0.2879 \cdot x \cdot y-0.4974 \cdot y^2+0.0201 \cdot x^3+0.0121 \cdot x^2 \cdot y-0.0027 \cdot x \cdot y^2+0.0213 \cdot y^3-0.0195 \cdot x^4-0.0061 \cdot x^3 \cdot y+0.0379 \cdot x^2 \cdot y^2+0.1243 \cdot x \cdot y^3+0.1041 \cdot y^4-0.0102 \cdot x^3-0.0052 \cdot x^4 \cdot y-0.0047 \cdot x^3 \cdot y^2+0.0137 \cdot x^2 \cdot y^3+0.0411 \cdot x \cdot y^4+0.0214 \cdot y^5$$

The t2 distribution fingerprint spectrum of the commercially available goat milk (FIG. 20) can be obtained by subtracting the reference surface F(x,y) from $f_n (\tau_1, n)$.

Example 18—The t2 distribution fingerprint spectrum of a pig hide gelatin

Sample: a pig hide gelatin.
NMR Instrument: VTMR20-010V-I relaxometry, Niumag Corp., Ltd., Shanghai, China. The Bo field is 0.5±0.05 T and the $^1$H Larmor frequency is 21.3 MHz. The experimental temperature is room temperature.

Method: The pulse sequence used in this experiment is shown in FIG. 2. In the experiment, $\tau_1$ was set to 100 μs, 200 μs, 300 μs, 400 μs, 500 μs, 650 μs and 800 μs, $\tau_2$ was set to 20 μs and $\tau_3$ was set to 200 ms. The number of repetition, n, was set to 3, 5, 10, 20, 40, 80, 100, 150, 200, 250, 300, 400, 500, 700, 900, 1200, 1500, and 2500. The two-dimensional relaxation surface f($\tau_1$, n) of the pig hide gelatin was obtained, which then was normalized to $f_n (\tau_1, n)$.

In this example, the reference surface function was obtained by fitting and normalizing the average value of two-dimensional relaxation surface $f_n(\tau_1, n)$ of the pig hide gelatin and cow hide gelatin. The reference surface function is:

$$F(x,y)=-0.2675-0.1528 \cdot x-0.3691 \cdot y-0.0574 \cdot x^2-0.2720 \cdot x \cdot y-0.4243 \cdot y^2-0.0024 \cdot x^3-0.0270 \cdot x^2 \cdot y-0.0552 \cdot x \cdot y^2-0.0768 \cdot y^3+0.00054 \cdot x^4+0.0133 \cdot x^3 \cdot y+0.0302 \cdot x^2 \cdot y^2+0.1050 \cdot x \cdot y^3+0.0899 \cdot y^4-0.00077 \cdot x^5+0.0025 \cdot x^4 \cdot y+0.0071 \cdot x^3 \cdot y^2+0.0280 \cdot x^2 \cdot y^3+0.0402 \cdot x \cdot y^4+0.0299 \cdot y^5$$

The t2 distribution fingerprint spectrum of the pig hide gelatin sample (FIG. 21) can be obtained by subtracting the reference surface F(x,y) from $f_n (\tau_1, n)$.

Example 19—the t2 Distribution Fingerprint Spectrum of a Cow Hide Gelatin

Sample: a cow hide gelatin.
NMR Instrument: VTMR20-010V-I relaxometry, Niumag Corp., Ltd., Shanghai, China. The Bo field is 0.5±0.05 T and the $^1$H Larmor frequency is 21.3 MHz. The experimental temperature is room temperature.

Method: The pulse sequence used in this experiment is shown in FIG. 2. In the experiment, $\tau_1$ was set to 100 μs, 200 μs, 300 μs, 400 μs, 500 μs, 650 μs and 800 μs, $\tau_2$ was set to 20 μs and $\tau_3$ was set to 200 ms. The number of repetition, n, was set to 3, 5, 10, 20, 40, 80, 100, 150, 200, 250, 300, 400, 500, 700, 900, 1200, 1500, and 2500. The two-dimensional relaxation surface f($\tau_1$, n) of the cow hide gelatin was obtained, which then was normalized to $f_n(\tau_1, n)$.

In this example, the reference surface function was obtained by fitting and normalizing the average of two-dimensional relaxation surface $f_n(\tau_1, n)$ of the pig hide gelatin and cow hide gelatin. The reference surface function is:

$$F(x,y)=-0.2675-0.1528 \cdot x-0.3691 \cdot y-0.0574 \cdot x^2-0.2720 \cdot x \cdot y-0.4243 \cdot y^2-0.0024 \cdot x^3-0.0270 \cdot x^2 \cdot y-0.0552 \cdot x \cdot y^2-0.0768 \cdot y^3+0.00054 \cdot x^4+0.0133 \cdot x^3 \cdot y+0.0302 \cdot x^2 \cdot y^2+0.1050 \cdot x \cdot y^3+0.0899 \cdot y^4-0.00077-x^5+0.0025 \cdot x^4 \cdot y+0.0071 \cdot x^3 \cdot y^2+0.0280 \cdot x^2 \cdot y^3+0.0402 \cdot x \cdot y^4+0.0299 \cdot y^5$$

The t2 distribution fingerprint spectrum of the cowhide gelatin sample (FIG. 22) can be obtained by subtracting the reference surface F(x,y) from $f_n(\tau_1, n)$.

Example 20—the t2 Distribution Fingerprint Spectrum of Liaoning Scorpion Powder Solution Sample: Liaoning scorpion powder solution. The weight ratio between the scorpion powder and the water is 1:1.
NMR Instrument: VTMR20-010V-I relaxometry, Niumag Corp., Ltd., Shanghai, China. The Bo field is 0.5±0.05 T and the $^1$H Larmor frequency is 21.3 MHz. The experimental temperature is room temperature.

Method: The pulse sequence used in this experiment is shown in FIG. 2. In the experiment, $\tau_1$ was set to 100 μs, 200 μs, 300 μs, 400 μs, 500 μs, 650 μs and 800 μs, $\tau_2$ was set to 20 μs and $\tau_3$ was set to 200 ms. The number of repetition, n, was set to 3, 5, 10, 20, 40, 80, 100, 150, 200, 250, 300, 400, 500, 700, 900, 1200, 1500, and 2500. The two-dimensional relaxation surface f($\tau_1$, n) of the Liaoning scorpion powder solution was obtained, which then was normalized to $f_n(\tau_1, n)$.

In this example, the reference surface function was obtained by fitting and normalizing the average value of the two-dimensional relaxation surface $f_n(\tau_1, n)$ of the Liaoning scorpion powder solution and the Shanxi scorpion powder solution. The reference surface function is:

$$F(x,y)=-0.2675-0.1528 \cdot x-0.3691 \cdot y-0.0574 \cdot x^2-0.2720-x-y-0.4243 \cdot y^2-0.0024 \cdot x^3-0.0270-x^2 \cdot y-0.0552 \cdot x-y^2-0.0768-y^3+0.00054 \cdot x^4+0.0133 \cdot x^3 \cdot y+0.0302 \cdot x^2 \cdot y^2+0.1050 \cdot x \cdot y^3+0.0899 \cdot y^4-0.00077 \cdot x^5+0.0025 \cdot x^4 \cdot y+0.0071 \cdot x^3 \cdot y^2+0.0280 \cdot x^2 \cdot y^3+0.0402 \cdot x \cdot y^4+0.0299 \cdot y^5$$

The t2 distribution fingerprint of Liaoning scorpion powder solution (FIG. 23) can be obtained by subtracting the reference surface F(x,y) from $f_n(\tau_1, n)$.

Example 21—the t2 Distribution Fingerprint Spectrum of Shanxi Scorpion Powder Solution Sample: Shanxi scorpion powder solution. The weight ratio between the scorpion powder and the water is 1:1.
NMR Instrument: VTMR20-010V-I relaxometry, Niumag Corp., Ltd., Shanghai, China. The Bo field is 0.5±0.05 T and the $^1$H Larmor frequency is 21.3 MHz. The experimental temperature is room temperature.

Method: The pulse sequence used in this experiment is shown in FIG. 2. In the experiment, $\tau_1$ was set to 100 μs, 200 μs, 300 μs, 400 μs, 500 μs, 650 μs and 800 μs, $\tau_2$ was set to 20 μs and $\tau_3$ was set to 200 ms. The number of repetition, n, was set to 3, 5, 10, 20, 40, 80, 100, 150, 200, 250, 300, 400, 500, 700, 900, 1200, 1500, and 2500. The two-dimensional relaxation surface f($\tau_1$, n) of the Shanxi scorpion powder solution was obtained, which then was normalized to $f_n(\tau_1, n)$.

In this example, the reference surface function was obtained by fitting and normalizing the average value of two-dimensional relaxation surface $f_n(\tau_1, n)$ of the Liaoning scorpion powder solution and the Shanxi scorpion powder solution. The reference surface function is:

$$F(x,y) = -0.2675 - 0.1528 \cdot x - 0.3691 \cdot y - 0.0574 \cdot x^2 - 0.2720 \cdot x \cdot y - 0.4243 \cdot y^2 - 0.0024 \cdot x^3 - 0.0270 \cdot x^2 \cdot y - 0.0552 \cdot x \cdot y^2 - 0.0768 \cdot y^3 + 0.00054 \cdot x^4 + 0.0133 \cdot x^3 \cdot y + 0.0302 \cdot x^2 \cdot y^2 + 0.1050 \cdot x \cdot y^3 + 0.0899 \cdot y^4 - 0.00077 \cdot x^3 + 0.0025 \cdot x^4 \cdot y + 0.0071 \cdot x^3 \cdot y^2 + 0.0280 \cdot x^2 \cdot y^3 + 0.0402 \cdot x \cdot y^4 + 0.0299 \cdot y^5$$

The t2 distribution fingerprint of Shanxi scorpion powder solution (FIG. 24) can be obtained by subtracting the reference surface $F(x,y)$ from $f_n(\tau_1, n)$.

The present invention has the following features which are different from previous methods and technologies:
1. Based on the feature that the $^1H$ $T_1$ and $T_2$ relaxation properties are different in different edible oils or other liquid-like samples, the method in the present invention breaks through the limitation of previous works using only $^1H$ $T_2$ relaxation to detect and identify edible oils or other liquid-like samples, innovatively proposes to amplify $^1H$ $T_1$ and $T_2$ relaxation differences of edible oils or other liquid-like samples by measuring two-dimensional $^1H$ $T_1$ and $T_2$ relaxation data containing relaxation properties of edible oils or other liquid-like samples, thus realize the detection and identification of edible oils or other liquid-like samples;
2. Based on the above idea, a new pulse sequence and the corresponding data acquisition method are developed to be used to amplify the $^1H$ $T_1$ and $T_2$ relaxation differences of different edible oils or other liquid-like samples;
3. A 'fingerprint spectrum' containing the $^1H$ $T_1$ and $T_2$ relaxation properties of edible oils or other liquid-like samples is constructed. The fingerprint can be used as a standard to distinguish different types of edible oil or other liquid-like samples, meanwhile, its digital form is very suitable for constructing the big data of edible oils or other liquid-like samples and the authenticity judgments based on artificial intelligence.
4. The method in the present invention can be used om high-resolution nuclear magnetic instruments and low-field magnetic resonance relaxometry, overcoming the dependence of the patent CN108982570A on the nuclear magnetic resonance signal resolution. At the same time, the measurement of $^1H$ $T_1$ and $T_2$ relaxation properties overcomes the low discrimination of the traditional method caused by only measuring the individual $^1H$ $T_2$ relaxation.
5. Compared with the traditional chromatographic, mass spectrometry and the optical spectroscopy, the method in the present invention can realize a non-destructive sample testing without sample pretreatment. The method can be implemented on a low-field magnetic resonance instrument which can achieve a rapid on-site detection by moving on board.

It should be understood that the term "and/or" used in the present invention is only to describe a relationship between associated objects, which means that there can be three relationships, i.e A and/or B can mean three conditions: A alone, A and B, and B alone. In addition, the character "/" in the present invention generally indicates that the associated objects before and after being in an 'or' relationship.

The protection of the present invention is not limited to the following embodiments. Without departing from the spirit and scope of the idea of the invention, all changes and advantages that can be thought of by a person skilled in the field are included in the present invention and are protected by the attached claims.

What is claimed:

1. A method for species identification and quality detection of liquid-like samples based on nuclear magnetic resonance technology comprising the following steps:
    step 1: designing a pulse sequence that includes pulse block or composite pulses containing $^1H$ spin-echo function and pulse block or composite pulses containing a $T_1$ filter function;
    step 2: applying the pulse sequence to the targeted liquid-like samples to obtain their $^1H$ two-dimensional relaxation signals;
    step 3: converting the obtained $^1H$ two-dimensional relaxation signals into a fingerprint spectra of the liquid-like samples, to be used for species identification and quality detection of liquid-like samples by obtaining $f_n(x,y)$ by normalizing the signal intensity of a two-dimensional relaxation signal $f(x,y)$ and subtracting reference function $F(x,y)$ from $f_m(x,y)$, wherein the reference function $F(x,y)$ is obtained from the $^1H$ relaxation properties of the sample, or from a surface fitting of $f_n(x,y)$, or averaging $F_m(x, y)$, m=1, 2, . . . , i, which is acquired from surface fitting of the multiple two-dimensional relaxation signals.

2. The method of claim 1, wherein the pulse sequence in step 2) is applied to the liquid-like samples and said liquid like sampled comprise at least one of: edible oil, cow and goat milk, donkey-hide gelatin, scorpion powder solution, yogurt, beverage, non-edible oil.

3. The method of claim 1, wherein, in step 1, the pulse sequence comprises the following sub-steps:
    step 1-1: using a pulse block or composite pulses to excite $^1H$ magnetic resonance signal of the system under test;
    step 1-2: applying the pulse block or the composite pulses containing $^1H$ spin-echo function to the system under test, wherein the pulse block or the composite pulses may contain one or more variables;
    step 1-3: applying the pulse block or the composite pulses containing $^1H$ $T_1$ filter function to the system under test, wherein the pulse block or the composite pulses may contain one or more variables;
    step 1-4: converting the $^1H$ magnetic resonance signal of the liquid-like samples into a signal detectable by magnetic resonance instrument through the pulse block or the composite pulses, and then collecting the signals.

4. The method of claim 1, wherein in the said pulse sequence:
    in step 1), a $^1H$ magnetic resonance signal of the system is excited with a 90° pulse with a phase of x;
    in step 2), a composite pulse block $[\tau_1-(180°)_y-\tau_1]_n$, is applied wherein n is the number of repetitions $\tau_1$ is the time variable;
    step 3), a composite pulse block $[\tau_2-(90°)_x-\tau_3]$ is applied, wherein $\tau_2$ is the time constant ranging from 10 μs to 20 μs, and $\tau_3$ is the time variable; and
    further comprising a step 4, wherein the $^1H$ magnetic resonance signal of the system under is converted into a signal detectable by magnetic resonance instrument with a 90° pulse with the phases of x, y, −x, −y, and signals are collected.

5. The method of claim 1, wherein, in step 2, the $^1H$ two-dimensional relaxation signal of the sample is obtained by controlling the variables in the pulse block or the composite pulses containing $^1H$ spin-echo function and the variables in the pulse block or the composite pulses containing $\tau_1$ filter function in the pulse sequence.

6. The method of claim 1, wherein, when comparing the fingerprint spectrum for species identification and quality detection of liquid-like samples of the same type, the same reference function is used in the generation process of fingerprint spectrum in step 3) for species belonging to the same liquid-like sample type but in different qualities.

7. The method of claim 1, wherein, when using the above-mentioned pulse sequence to acquire the two-dimensional relaxation signal of the liquid-like sample and the liquid-like sample is corn germ oil, the two-dimensional relaxation signal of corn germ oil, $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the $\tau_2$ distribution fingerprint spectrum of corn germ oil is obtained by subtracting the selected reference function F(x, y) from the normalized $f(\tau_1, n)$; and/or, when using the above-mentioned pulse sequence to acquire the two-dimensional relaxation signal of the liquid-like sample and the liquid-like sample is peanut oil, the two-dimensional relaxation signal of peanut oil $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the t2 distribution fingerprint spectrum of peanut oil is obtained by subtracting the selected reference function F(x, y) from the normalized $f(\tau_1, n)$; and/or, when using the above-mentioned pulse sequence to acquire the two-dimensional relaxation signal of the liquid-like sample and the liquid-like sample is soybean oil, the two-dimensional relaxation signal of soybean oil $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the t2 distribution fingerprint spectrum of soybean oil is obtained by subtracting the selected reference function F(x, y) from the normalized $f(\tau_1, n)$; and/or, when using the above-mentioned pulse sequence to acquire the two-dimensional relaxation signal of the liquid-like sample and the liquid-like sample is linseed oil, the two-dimensional relaxation signal of linseed oil $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the t2 distribution fingerprint spectrum of linseed oil is obtained by subtracting the selected reference function F(x, y) from the normalized $f(\tau_1, n)$; and/or, when using the above-mentioned pulse sequence to acquire the two-dimensional relaxation signal of the liquid-like sample and the liquid-like sample is olive oil, the two-dimensional relaxation signal of olive oil $f(\tau_1, n)$ can be obtained by fixing $\tau_3$ and changing $\tau_1$ and n, wherein $\tau_1$ is a set of time values and n is cycle number, $f(\tau_1, n)$ is the signal intensity corresponding to $\tau_1$ and n; the t2 distribution fingerprint spectrum of olive oil is obtained by subtracting the selected reference function F(x, y) from the normalized $f(\tau_1, n)$; and/or, when using the above-mentioned pulse sequence to acquire the two-dimensional relaxation signal of the liquid-like sample and the liquid-like sample is commercially available cow milk, the two-dimensional relaxation signal of the commercially available cow milk $f(\tau_1, n)$ can be obtained by fixing $\tau_3$ and changing $\tau_1$ and n, wherein $\tau_1$ is a set of time values, n is a set of cycle number, $f(\tau_1, n)$ is the signal intensity corresponding to $\tau_1$ and n; the $\tau_2$ distribution fingerprint spectrum of the commercially available cow milk is obtained by subtracting the selected reference function F(x, y) from the normalized $f(\tau_1, n)$; and/or, when using the above-mentioned pulse sequence to acquire the two-dimensional relaxation signal of the liquid-like sample and the liquid-like sample is commercially available goat milk, the two-dimensional relaxation signal of the commercially available goat milk $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the $\tau_2$ distribution fingerprint spectrum of the commercially available goat milk is obtained by subtracting the selected reference function F(x, y) from the normalized $f(\tau_1, n)$; and/or, when using the above-mentioned pulse sequence to acquire the two-dimensional relaxation signal of the liquid like sample and the liquid-like sample is pig hide gelatin, the two-dimensional relaxation signal of pig hide gelatin $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the t2 distribution fingerprint spectrum of pig hide gelatin is obtained by subtracting the selected reference function F(x, y) from the normalized $f(\tau_1, n)$; and/or, when using the above-mentioned pulse sequence to acquire the two-dimensional relaxation signal of the liquid sample and the liquid-like sample is cow hide gelatin, the two-dimensional relaxation signal of cow hide gelatin $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the t2 distribution fingerprint spectrum of cow hide gelatin is obtained by subtracting the selected reference function F(x, y) from the normalized $f(\tau_1, n)$; and/or, when using the above-mentioned pulse sequence to acquire the two-dimensional relaxation signal of the liquid-like sample and the liquid-like sample is Liaoning scorpion powder solution, the two-dimensional relaxation signal of Liaoning scorpion powder solution $f(\tau_1, n)$ can be obtained by fixing $\tau_3$ and changing $\tau_1$ and n, wherein $\tau_1$ is a set of time values and n is cycle number, $f(\tau_1, n)$ is the signal intensity corresponding to $\tau_1$ and n; the $\tau_2$ distribution fingerprint spectrum of Liaoning scorpion powder solution is obtained by subtracting the selected reference function F(x, y) from the normalized $f(\tau_1, n)$; and/or, when using the above-mentioned pulse sequence to acquire the two-dimensional relaxation signal of the liquid-like sample and the liquid-like sample is Shanxi scorpion powder solution, the two-dimensional relaxation signal of Shanxi scorpion powder solution $f(\tau_1, n)$ can be obtained by fixing $\tau_3$ and changing $\tau_1$ and n, wherein $\tau_1$ is a set of time values, n is cycle number, $f(\tau_1, n)$ is the signal intensity corresponding to $\tau_1$ and n; the t2 distribution fingerprint spectrum of Shanxi scorpion powder solution is obtained by subtracting the selected reference function F(x, y) from the normalized $f(\tau_1, n)$.

8. The method of claim 1, wherein, when using the above-mentioned pulse sequence to acquire the two-dimensional relaxation signal of the liquid-like sample and the liquid-like sample is corn germ oil, the two-dimensional relaxation signal of corn germ oil $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of corn germ oil is obtained by subtracting the selected reference function $F_a(x, y)$ from the normalized $f_a(\tau_3, n)$; and/or, when using the above-mentioned pulse sequence to acquire the two-dimensional relaxation signal of liquid-like sample and the liquid-like sample is peanut oil, the two-dimensional relaxation signal of peanut oil $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of peanut oil is obtained by subtracting the selected reference function $F_a(x, y)$ from the normalized $f_a(\tau_3, n)$; and/or, when using the above-mentioned pulse sequence to acquire the two-dimensional relaxation signal of the liquid-like sample and the liquid-like sample is soybean oil, the two-dimensional relaxation signal of soybean oil $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of soybean oil is obtained by subtracting the selected reference function $F_a(x, y)$ from the normalized $f_a(\tau_3, n)$; and/or, when using the above-mentioned pulse sequence to acquire the two-dimensional relaxation signal of the liquid-like sample and liquid-like sample is linseed oil, the two-dimensional relaxation signal of linseed oil $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of linseed oil is obtained by subtracting the selected reference function $F_a(x, y)$ from the normalized $f_a(\tau_3, n)$; and/or, when using the above-mentioned pulse sequence to acquire the two-dimensional relaxation signal of the liquid-like sample and the liquid-like sample is olive oil, the two-dimensional relaxation signal of olive oil $f_a(\tau_3, n)$ can be obtained by fixing $\tau_1$ and meanwhile changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of olive oil is obtained by subtracting the selected reference function $F_a(x, y)$ from the normalized $f_a(\tau_3, n)$; and/or, when using the above-mentioned pulse sequence to acquire the two-dimensional relaxation signal of the liquid-like sample mixed with 1% water by weight, the two-dimensional relaxation signal of the liquid-like sample mixed with 1% water by weight $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of the liquid-like sample mixed with 1% water by weight is obtained by subtracting the selected reference function $F_a(x, y)$ from the normalized $f_a(\tau_3, n)$; and/or, when using the above-mentioned pulse sequence to acquire the two-dimensional relaxation signal of the liquid-like sample mixed with 1% lard by weight, the two-dimensional relaxation signal of the liquid-like sample mixed with 1% lard by weight $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of the liquid-like sample mixed with 1% lard by weight is obtained by subtracting the selected reference function $F_a(x, y)$ from the normalized $f_a(\tau_3, n)$; and/or, when using the above-mentioned pulse sequence to acquire the two-dimensional relaxation signal of the liquid-like sample mixed with 1% beef tallow by weight, the two-dimensional relaxation signal of the liquid-like sample mixed with 1% beef tallow by weight $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $\tau_1$-$\tau_2$ correlation fingerprint spectrum of the liquid-like sample mixed with 1% beef tallow by weight is obtained by subtracting the selected reference function $F_a(x, y)$ from the normalized $f_a(\tau_3, n)$; and/or, when using the above-mentioned pulse sequence to acquire the two-dimensional relaxation signal of the c liquid-like sample mixed with 1% butter by weight, the two-dimensional relaxation signal of the sample mixed with 1% butter by weight $f_a(\tau_3, n)$ can be obtained by fixing $\tau_1$ and changing $\tau_3$ and n, wherein $\tau_3$ is a set of time values, n is cycle number, $f_a(\tau_3, n)$ is the signal intensity corresponding to $\tau_3$ and n; the $t_1$-$t_2$ correlation fingerprint spectrum of the liquid-like sample mixed with 1% butter by weight is obtained by subtracting the selected reference function $F_a(x, y)$ from the normalized $f_a(\tau_3, n)$.

\* \* \* \* \*